US007329423B2

(12) United States Patent  
Andersen et al.

(10) Patent No.: US 7,329,423 B2  
(45) Date of Patent: Feb. 12, 2008

(54) COMPOSITIONS COMPRISING THYLAKOIDS USEFUL IN THE MODULATION OF INFLAMMATION PROCESS

(75) Inventors: Alain Andersen, Saint-Etienne-de-Lauzon (CA); Elyse Bissonnette, Sainte-Foy (CA); Rejean Drouin, Trois-Rivieres (CA); Marc Purcell, Saint-Augustin-de-Desmaures (CA)

(73) Assignee: Purecell Technologies Inc., Quebec (CA)

( * ) Notice: Subject to any disclaimer, the term of this patent is extended or adjusted under 35 U.S.C. 154(b) by 468 days.

(21) Appl. No.: 10/482,797

(22) PCT Filed: Jul. 2, 2002

(86) PCT No.: PCT/CA02/01009

§ 371 (c)(1),  
(2), (4) Date: Oct. 28, 2004

(87) PCT Pub. No.: WO03/004042

PCT Pub. Date: Jan. 16, 2003

(65) Prior Publication Data

US 2005/0048148 A1    Mar. 3, 2005

Related U.S. Application Data

(60) Provisional application No. 60/301,832, filed on Jul. 2, 2001.

(30) Foreign Application Priority Data

Apr. 15, 2002    (CA) .................... 2381830

(51) Int. Cl.  
*A61K 35/78* (2006.01)  
*A61K 8/00* (2006.01)  
*C12N 1/00* (2006.01)

(52) U.S. Cl. ............... 424/774; 424/59; 435/317.1; 514/886; 514/887

(58) Field of Classification Search ............ None  
See application file for complete search history.

(56) References Cited

U.S. PATENT DOCUMENTS

2003/0175374 A1* 9/2003 Purcell

FOREIGN PATENT DOCUMENTS

WO    WO 01/49305    7/2001

OTHER PUBLICATIONS

Linden M. et al. American Journal of Respiratory and Critical Care Medicine, (Nov. 2000) vol. 162, No. 5, pp. 1705-1708. Immediate effect of topical budesonide on allergen challenge-induced nasal mucosal fluid levels of granulocyte-macrophage colony-stimulating factor and interleukin-5.*

Wilgus, T. et al. Prostaglandins and Other Lipid Mediators, (Oct. 2000) vol. 62, No. 4, pp. 367-384. Topical application of a selective cyclooxygenase inhibitor suppresses UVB mediated cutaneous inflammation. Abstract.*

Barnes, PG, and Lim, S. 1998. "Inhibitory cytokines in asthma". Mol. Med. Today. Oct., pp. 452-458.

Berg DJ, Leach MW, Kuhn R, Rajewsky K, Muller W, Davidson NJ, Rennick D.1995. "Interleukin 10 but not interleukin 4 is a natural suppressant of cutaneous inflammatory responses". J Exp Med. vol. 182 p. 182:99-108.

Brink, N, Szamel, M, Young, AR, Wittern, KP, and Bergemann, J. 2000. "Comparative quantification of IL-10β, IL-10, IL-10r, TNF-α and IL-7 mRNA levels in UV-irradiated human skin in vivo". Inflamm. Res. 49:290-296.

Crystal, RG. 1991. "Alveolar macrophages". In: Crystal, RG and Weast, JB, (eds). The lung: Scientific Foundation. Raven Press, NY. pp. 527-538.

Daemen, MA, van de Ven, MW, Heineman, E, Buurman, WA. 1999. "Involvement of endogenous interleukin-10 and tumor necrosis factor-alpha in renal ischemia-reperfusion injury". Transplantation 67:792-800.

Deckert M, Soltek S, Geginat G, Lutjen S, Montesinos-Rongen M, Hof H, Schluter D. 2001. "Endogenous Interleukin-10 Is Required for Prevention of a Hyperinflammatory Intracerebral Immune Response in Listeria monocytogenes Meningoencephalitis". Infect Immun. 69:4561-4571.

Dionne S, D'Agata ID, Hiscott J, Vanounou T, Seidman EG. 1998. "Colonic explant production of IL-1 and its receptor antagonist is imbalanced in inflammatory bowel disease (IBD)". Clin Exp Immunol 112:435-442.

Feghali, CA, and Wright, TM. 1997. "Cytokines in acute and chronic inflammation". Front. Biosci. 1:d12-26.

Foye, WO. 1989. "Principals of Medicinal Chemistry". Lea and Febiger, London. Gasche C, Bakos S, Dejaco C, Tillinger W, Zakeri S, Reinisch W. 2000. "IL-10 secretion and sensitivity in normal human intestine and inflammatory bowel disease". J Clin Immunol. 20:362-70.

Griswold, DE, Martin, LD, Badger, AM, Breton, J, and Chabot-Fletcher, M. 1998. "Evaluation of the cutaneous anti-inflammatory activity of azaspiranes". Inflamm. Res. 47:56-61.

(Continued)

*Primary Examiner*—Michelle Flood  
(74) *Attorney, Agent, or Firm*—Nicholas A. Kees; Godfrey & Kahn S.C.

(57) ABSTRACT

A thylakoid extract that is preferably stabilized and activable for treating inflammation is described. Different types of cell or tissue targets and inflammatory stimuli have been used to evaluate the performance of the extract, which, in all cases successfully modulate inflammation through a balance of pro/anti-inflammatory cytokines. Compositions comprising the extract and other anti-inflammatory agents, such as glucocorticoids or non-steroidal anti-inflammatory drugs (NSAIDs) are further disclosed and claimed.

22 Claims, 19 Drawing Sheets

OTHER PUBLICATIONS

Gudmundsson, G, Bosch, A, Davidson, BL, Berg, DJ, Hunninghake, GW. 1998. "Interleukin-10 modulates the severity of hypersensitivity pneumonitis in mice". Am. J. Repir. Cell. Mol. Biol. 19:812-818.

Higgins LM, Frankel G, Douce G, Dougan G, MacDonald TT. 1999. "Citrobacter rodentium infection in mice elicits a mucosal Th 1 cytokine response to lesions similar to those in murine inflammatory bowel disease". Infect Immun 67:3031-3039.

Isakson, P. C. 1995. "Synthesis and Pharmacology of Selective Cox-2 Inhibitors" Med. Chem. Res. 5:344-350.

Jones, CA, Cayabyab, RG, Kwong, KY, Stotts, C, Wong, B, Hamdan, H, Minoo, P, deLemos, RA. 1996. "Undetectable interleukin (IL)-10 and persistent IL-8 expression early in hyaline membrane disease: a possible developmental basis for the predisposition to chronic lung inflammation in preterm newborns". Pediatr. Res. 39:966-975.

Kirsner JB, Shorter RG. 1995. "Inflammatory Bowel Disease". Chapter 3: 4th Edition; Williams and Wilkins, Maryland.

Kmiec Z. 1998. "Cytokines in inflammatory bowel disease". Arch Immuno Ther Exp (Warsz) 46:143-155.

Lee HJ, Lee HP, Ha SJ, Byun DG, Kim JW. 2000. "Spontaneous expression of mRNA for IL-10, GM-CSF, TGF-beta, TGF-alpha, and IL-6 in peripheral blood mononuclear cells from atopic dermatitis". Ann Allergy Asthma Immunol. 84:553-558.

Lewis, AJ and Manning, AM. 1999. "New targets for anti-inflammatory drugs". Curr. Opin. Chem. Biol. 3:489-494.

Maier, J. A. M., Hla, T., Macaig, "Cyclooxygenase Is an Immediate-early Gene Induced by Interleukin-1 in Human Endothelial Cells." T. J. 1990. J. Biol. Chem. 265:10805-10808.

Maini, RN, Elliot, M, Brennan, FM, Williams, RO, Feldmann, M. 1997. "TNF blockade in rheumatoid arthritis: implications for therapy and pathogenesis". APMIS 105:257-263.

Meade, LA, Smith, WI, DeWitt, "Differential Inhibition of Prostaglandin Endoperoxide Synthase (Cyclooxygenase) Isozymes by Aspirin and Other Non-steroidal Anti-inflammatory Drugs" DL. 1993. J Biol Chem 268:6610-6614.

Mitchell, JA, Akarasereenont, P, Thiemermann, C, Flowers, R, Vane, "Selectivity of nonsteroidal antiinflammatory drugs as inhibitors of constitutive and inducible cyclooxygenase" JR. 1993. P.N.A.S. 90:11693-11697.

Moriguchi M, Urabe K, Norisada N, Ochi C, Stalc A, Urleb U, Muraoka S. 1999. "Therapeutic effects of LK 423, a phthalimido-desmuramyl-dipeptide compound, on dextran sulfate sodium-induced colitis in rodents through restoring their interleukin-10 producing capacity". Arzneimittelforschung. 49:184-192.

Narula SK, Cutler D, Grint P. 1998. "Immunomodulation of Crohn's disease by interleukin-10". Agents Actions Suppl. 49:57-65. Review.

O'Sullivan, M. G., Chilton, F. H., Huggins, E. M., McCall. E. 1992. "Lipopolysaccharide priming of alveolar macrophages for enhanced synthesis of prostanoids involves induction of a novel prostaglandin H synthase" J. Biol. Chem. 267:14547-14550.

Pinto, D. J., Pitts, W. J., Copeland, R. A., Covington, M. B., Trzaskos, J., Magolda, R. 1995. "Selective inhibition of cyclooxygenase-2: Diaryl heterocycles vs Classical NSAIDS" Med. Chem. Res. 5:394-398.

Prasit, P., Black et al. "L-745,337: A selective cyclooxygenase-2 inhibitor". 1995. Med. Chem. Res. 5:364-374.

Raz, A., Wyche, A., Needleman, P. 1989."Temporal and pharmacological division of fibroblast cyclooxygenase expression into transcriptional and translational phase." P.N.A.S. 86:1657-1661.

Reich K, et al. 2001. "Response of psoriasis to interleukin-10 is associated with suppression of cutaneous type 1 inflammation, downregulation of the epidermal interleukin-8/CXCR2 pathway and normalization of keratinocyte maturation". J Invest Dermatol. 116:319-329.

Romay C, Ledon N, Gonzalez R. 1998. "Further studies on antiinflammatory activity of phycocyanin in some animal models of inflammation". Inflamm. Res. 47:334-338.

Sacca, R, Cuff, CA, and Ruddle, NH. 1997. "Mediators of inflammation". Curr. Opin. Immunol. 9:851-857.

Sartor RB. 1998. "The role of indigenous microflora in producing inflammation in inflammatory bowel disease". Research and Clinical Forum 20:117-123.

Sirois, P. 1985. "Pharmacology of the leukotrienes", Advances in Lipid Research, R. Paoletti, D. Kritchevsky (eds.) Academic Press, 21:79-101.

Stvrtinova, V, Jakubovsky, J, Hulin, I. 1995. "Inflammation and fever". Academic Electronic Press, Bratislava, Slovak Republic. 113 p.

Thomas, PS. 2001. "Tumor necrosis factor-alpha: The role of this multifunctional cytokine in asthma". Immunol Cell Biol. 79:132-140.

van Roon, JA, van Roy, JL, Gmelig-Meyling, FH, Lafeber, FP, Bijlsma, JW. 1996. "Prevention and reversal of cartilage degredation in rheumatoid arthritis by interleukin-10 and interleukin-4". J. Rheumatol. 39:829-835.

Whittle, B. J. R., Higgs, G. A., Eakins, K. E., Moncada, S., and Vane, J. R. "Selective inhibition of prostaglandine production in inflammatory exudates and gastric mucosa" 1980. Nature 284:271-273.

Yan XT, Zhuang M, Oakes JE, Lausch RN. 2001. "Autocrine action of IL-10 suppresses proinflammatory mediators and inflammation in the HSV-1-infected cornea". J Leukoc Biol. 69:149-157.

Torill Hundal, Patrik Forsmark-André e, Lars Ernster, and Bertil Andersson "Antioxidant acitivity of reduced plastoquinone in chloroplast thylakoid membranes." Archives of Biochemistry and Biophysics United States, vol. 324 No. 1, Dec. 1, 1995, pp. 117-122, XP002216090 ISSN: 0003-9861 Abstract page 121.

* cited by examiner

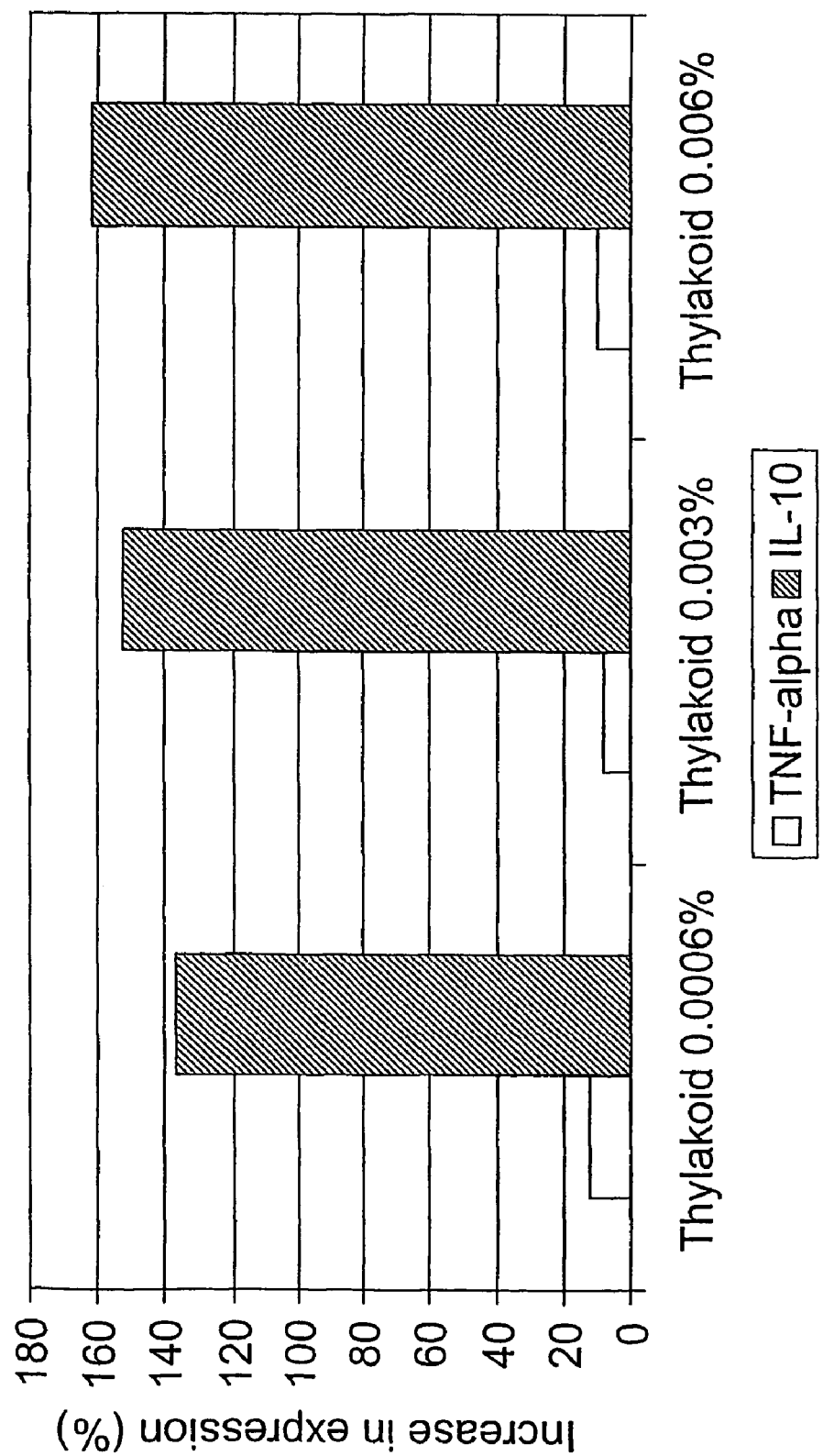
Fig. 1. Effect of thylakoid extract on cytokine expression (% relative to control) in alveolar macrophages when induced with LPS.

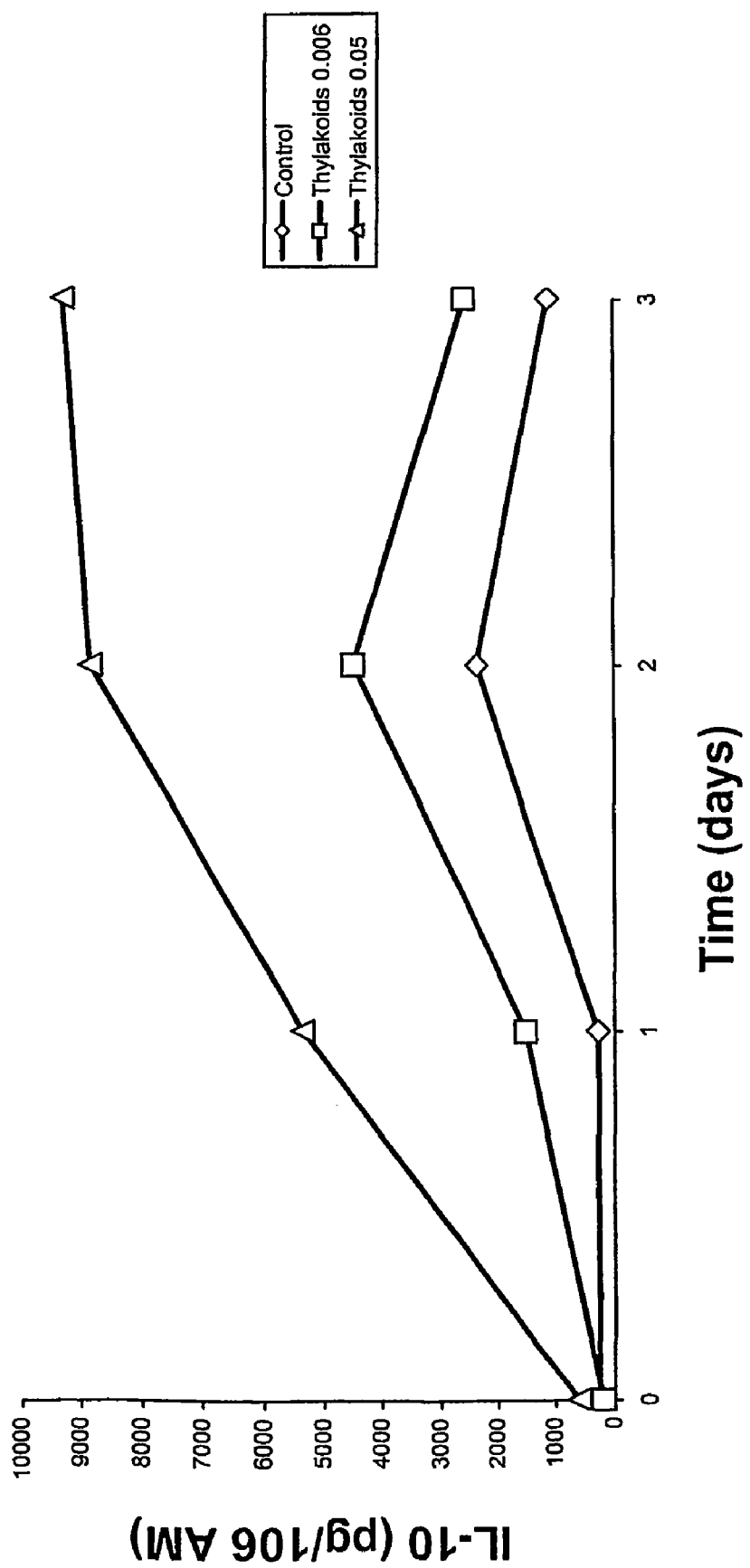
Fig. 2. Effect of pretreatment with thylakoid extract on IL-10 expression in LPS-stimulated alveolar macrophages

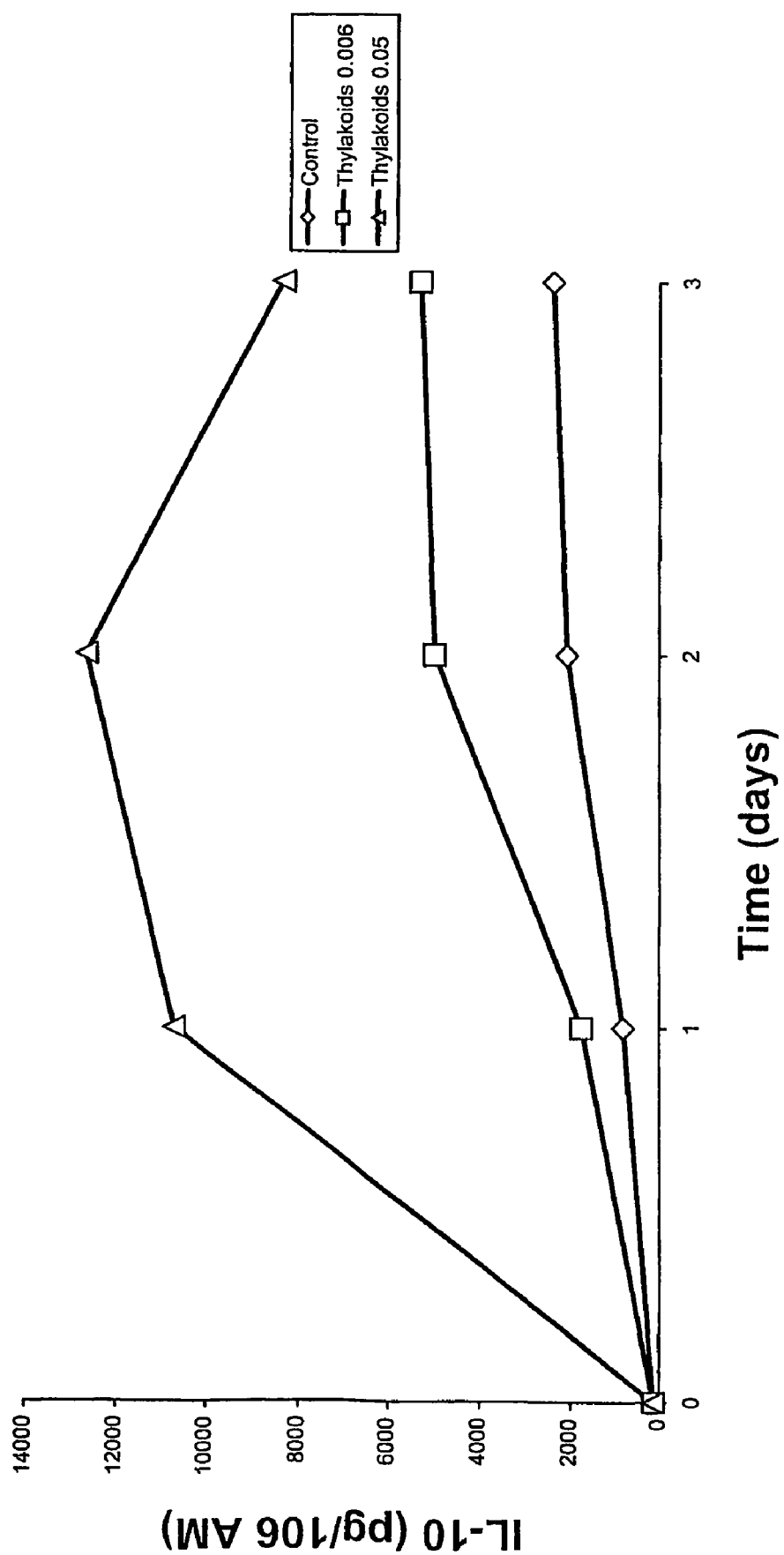
Fig. 3. Effect of post-treatment with thylakoid extract on IL-10 expression in LPS-stimulated alveolar macrophages

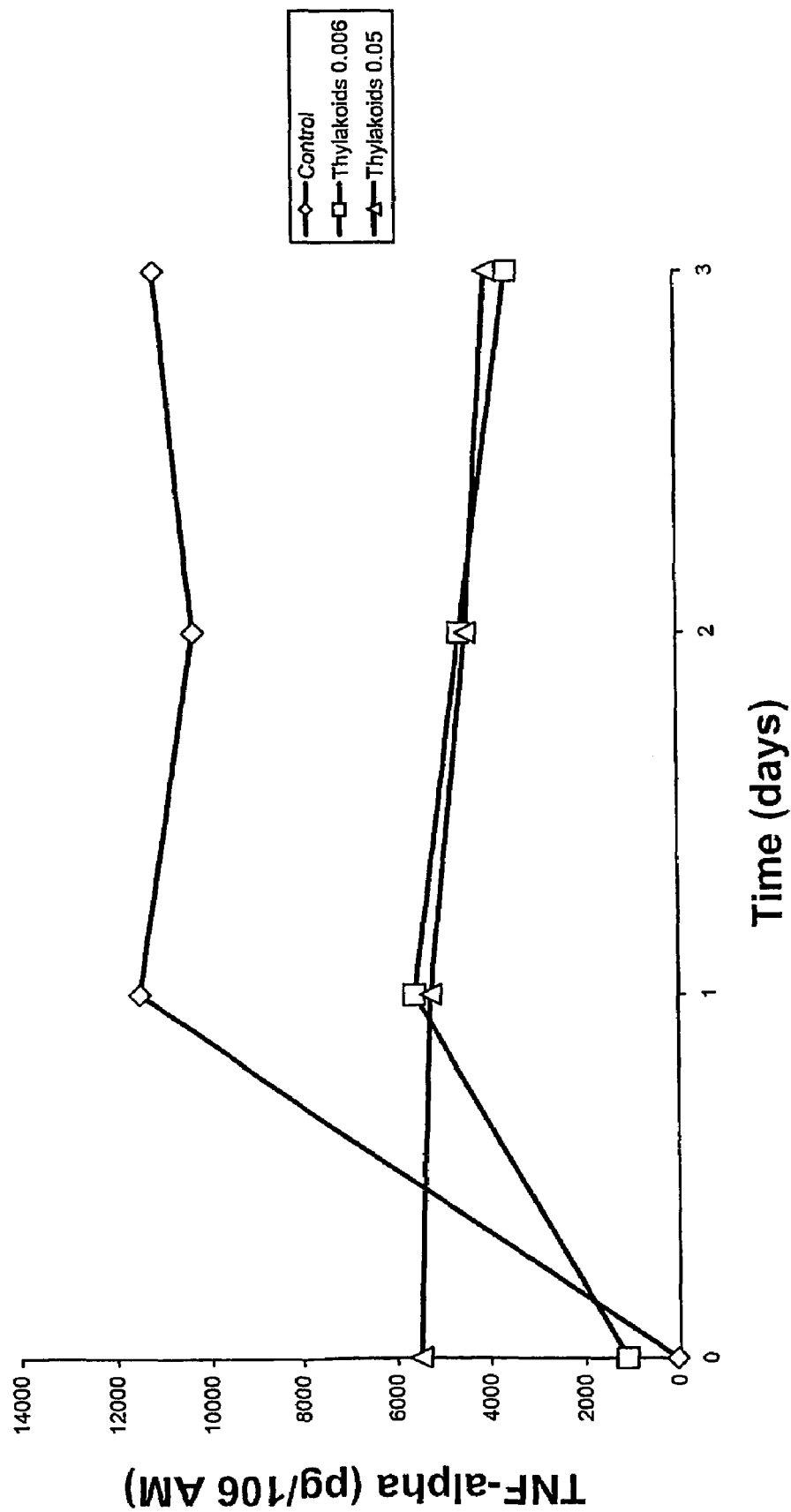
Fig. 4. Effect of pre-treatment with thylakoid extract on TNF-alpha expression in LPS-stimulated alveolar macrophages

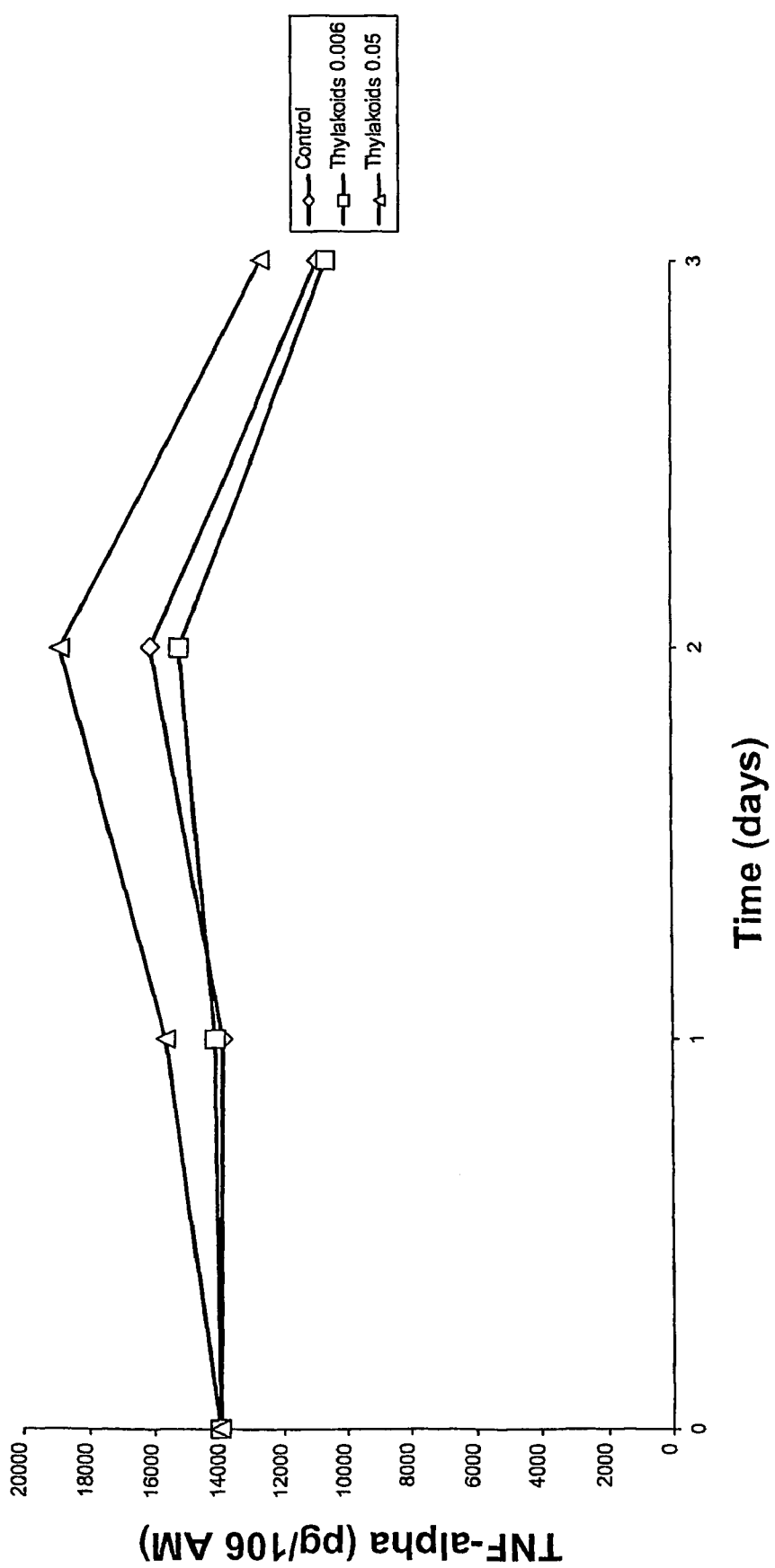
Fig. 5. Effects of post-treatment with thylakoid extract on TNF-alpha expression in LPS-stimulated alveolar macrophages

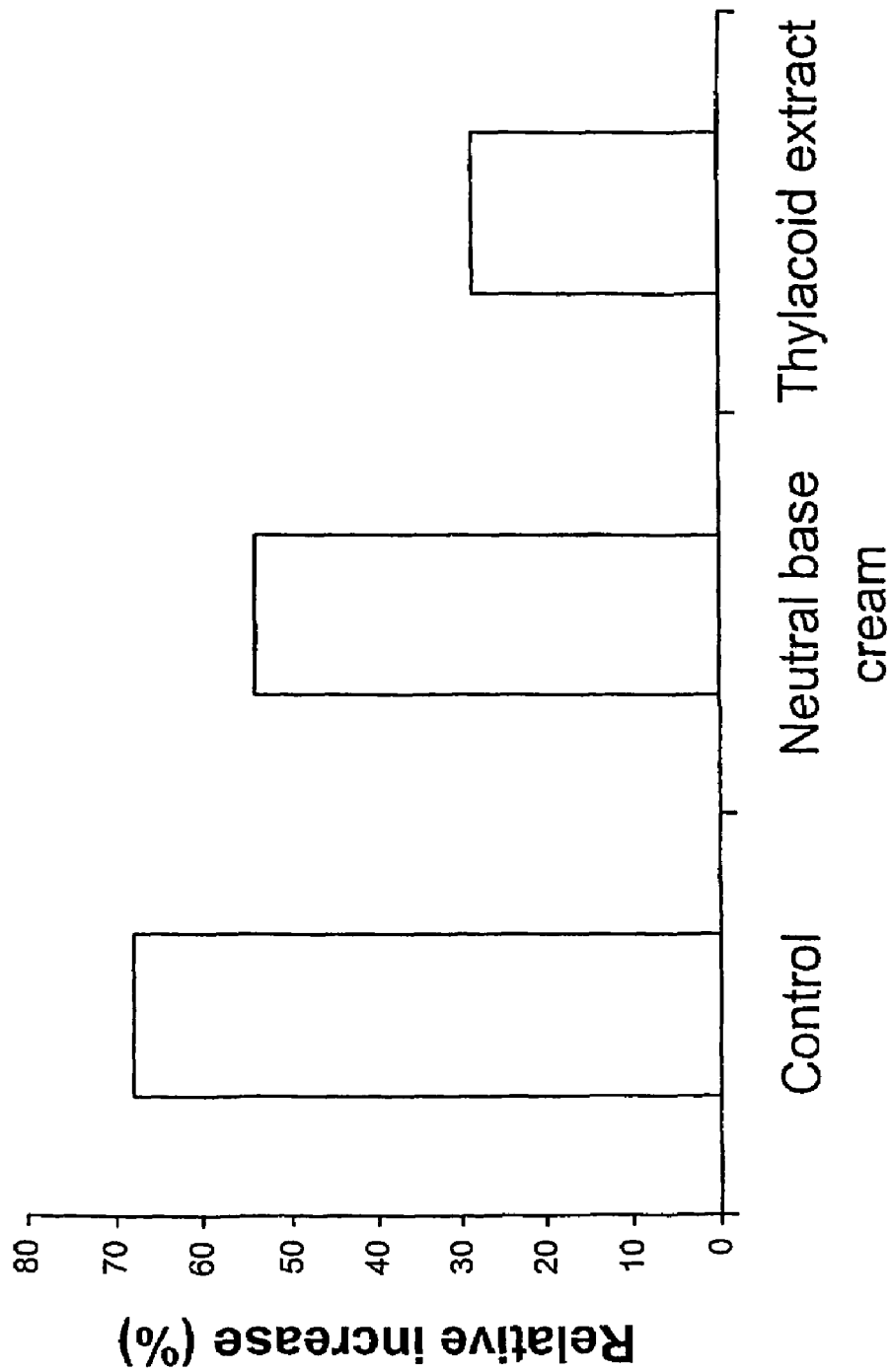
Fig. 6. Effect of thylakoid extract on the physical parameters of rat ear oedema following inflammation induced by arachidonic acid

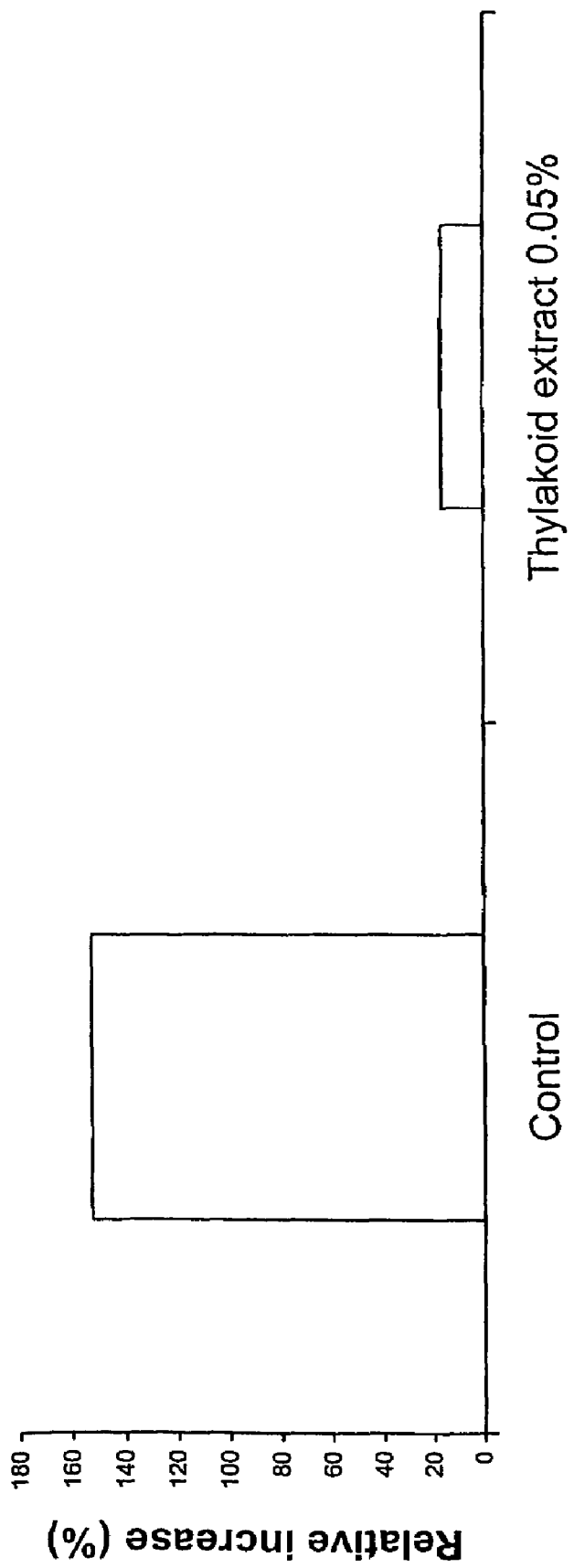
Fig. 7. Effect of thylakoid extract on the physical parameters of mouse ear oedema following inflammation induced by TPA

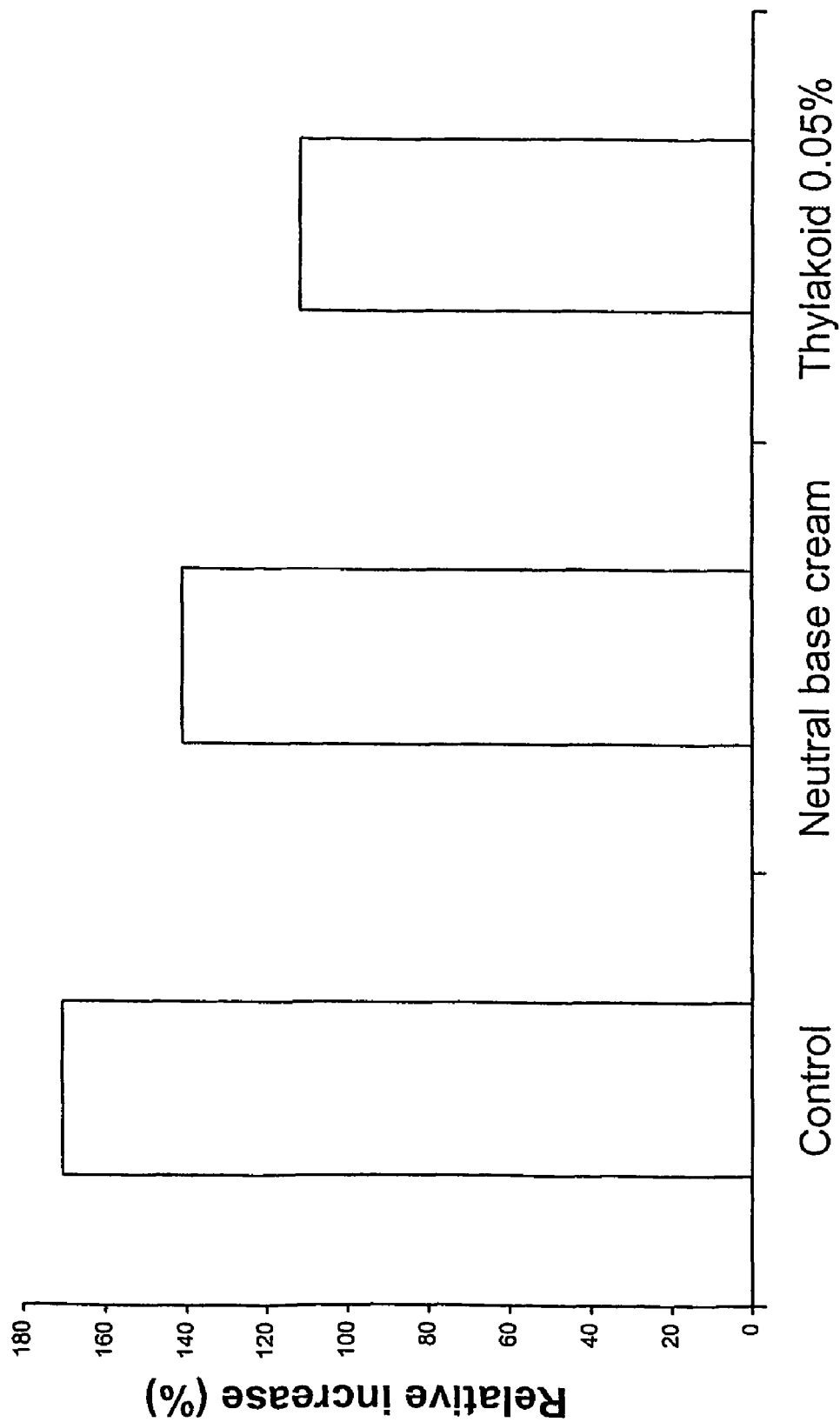
Fig. 8. Effect of thylakoid extract on the physical parameters (thickness) of TPA-induced mouse ear inflammation

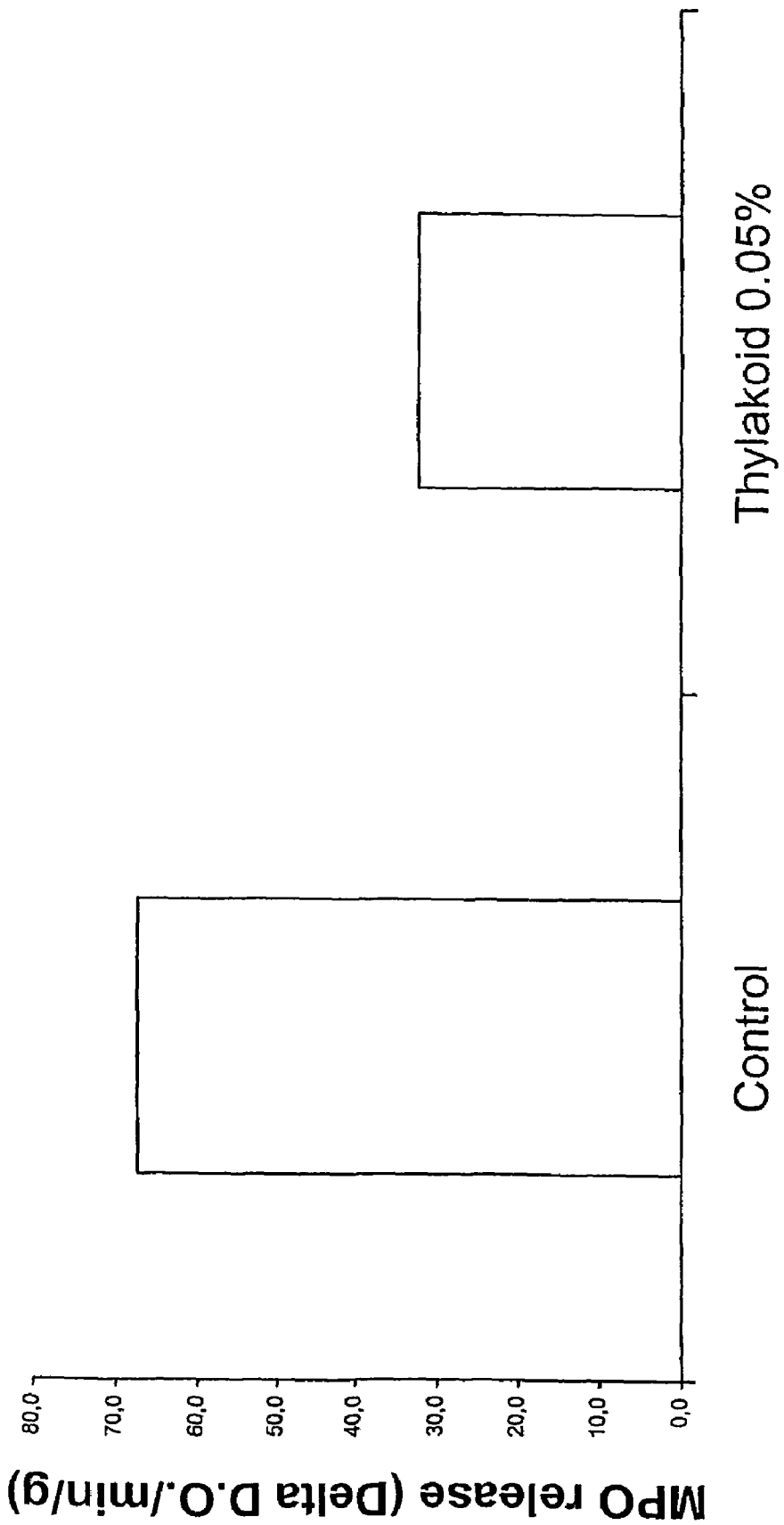
Fig. 9. Effect of thylakoid extract on myeloperoxidase release in TPA-induced mouse ear inflammation

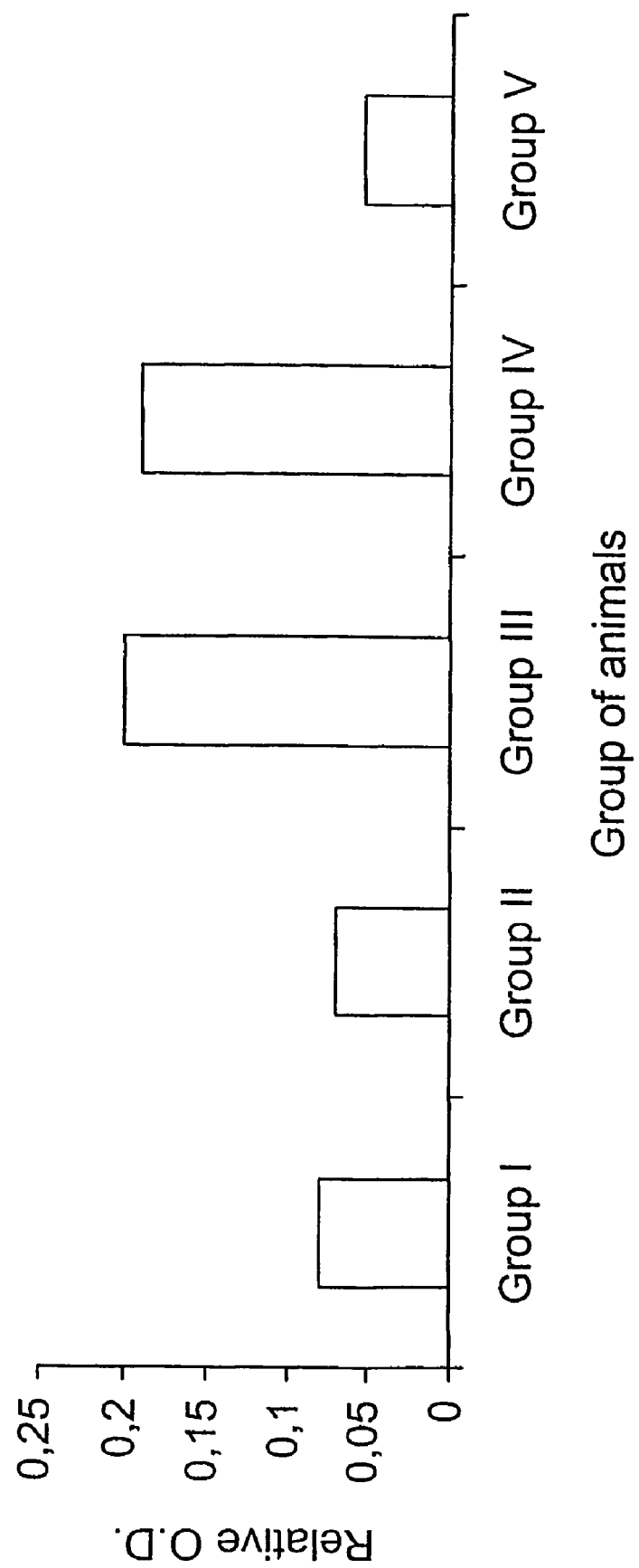
Fig. 10. Effect of thylakoid extract on TNF-alpha expression in mouse skin following inflammation induction by UV-irradiation

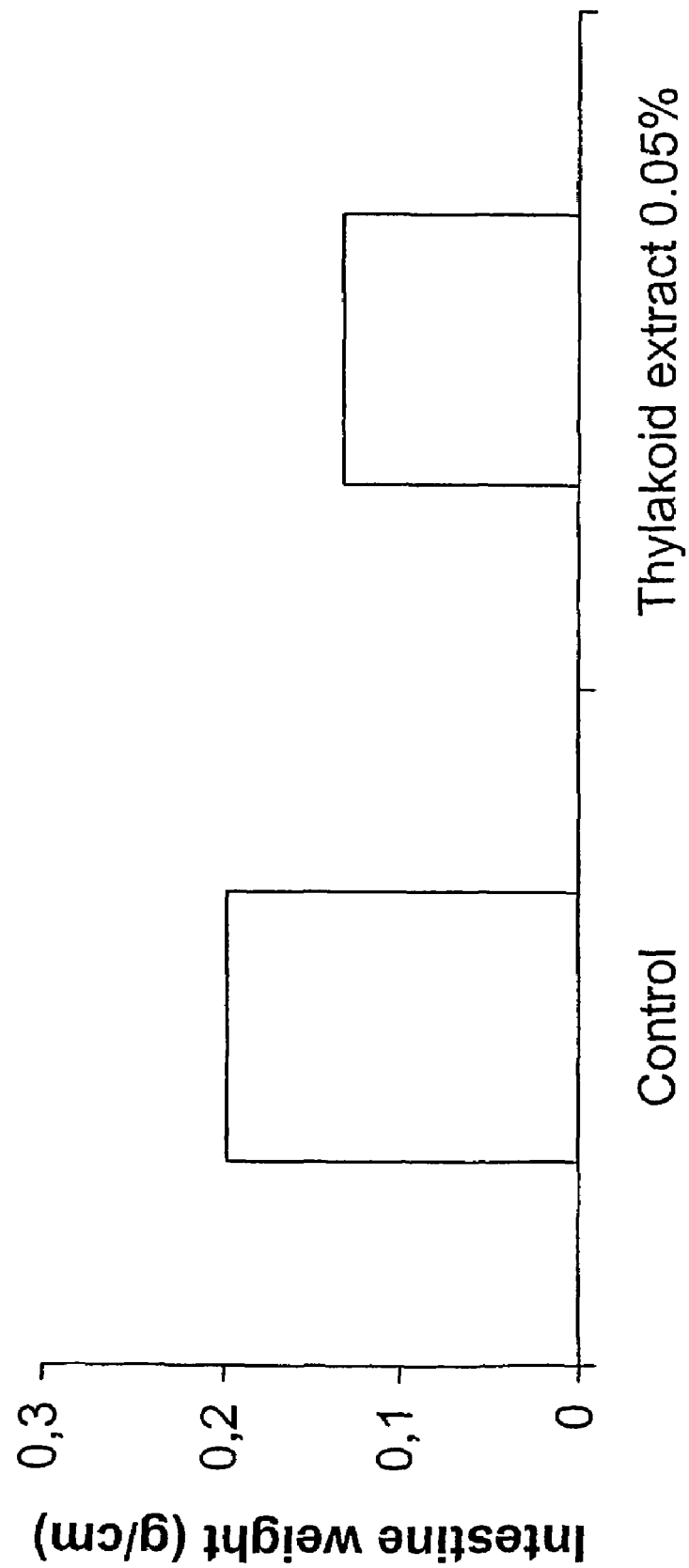
Fig. 11. Effect of intraperitoneal administration of thylakoid extract on weight of rat intestine induced by TNBS

Fig. 12. Effect of thylakoid extract on reducing TNBS-induced colonic damage
Protection against membrane alterations by thylakoid extract
Average colonic damage = 2.5 /10
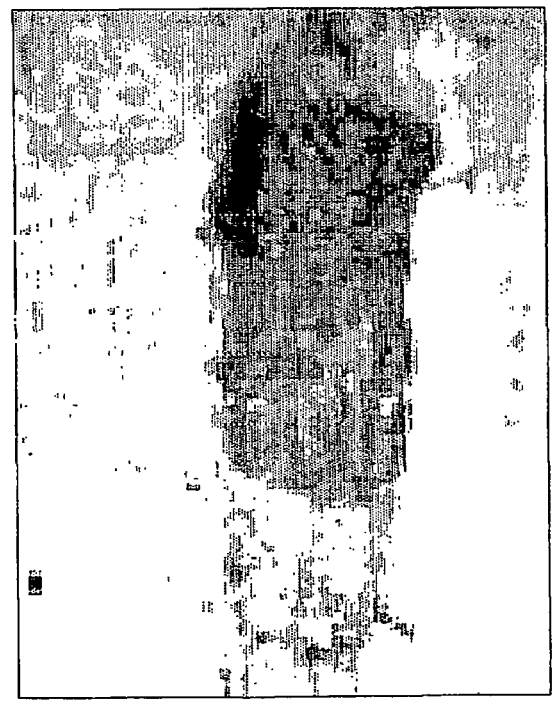
Macroscopic colonic damage induced by TNBS stress (control)
Average colonic damage = 5.5/10

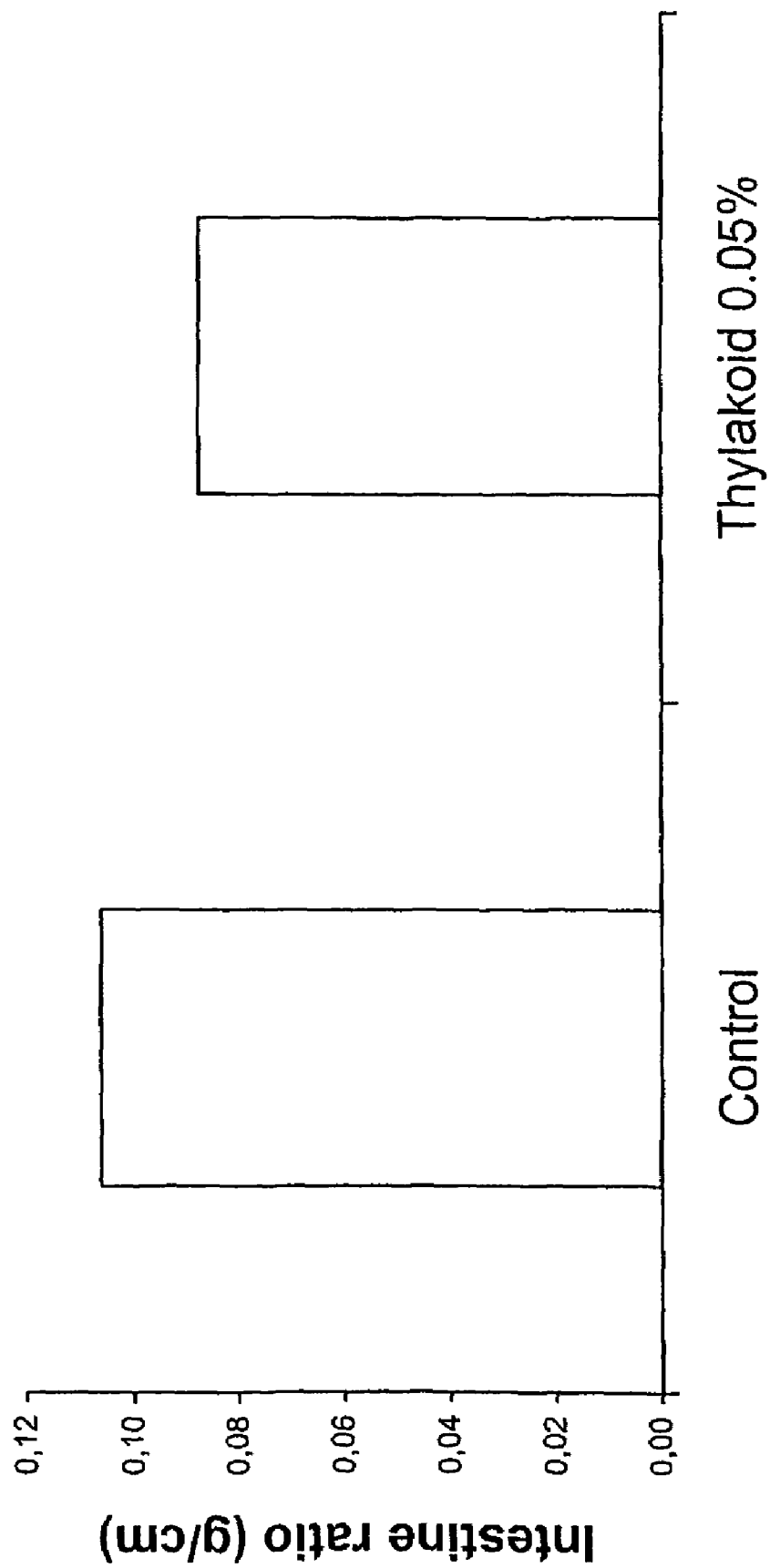
Fig. 13. Effect of thylakoid extract on the physical parameters of DSS-induced intestine inflammation

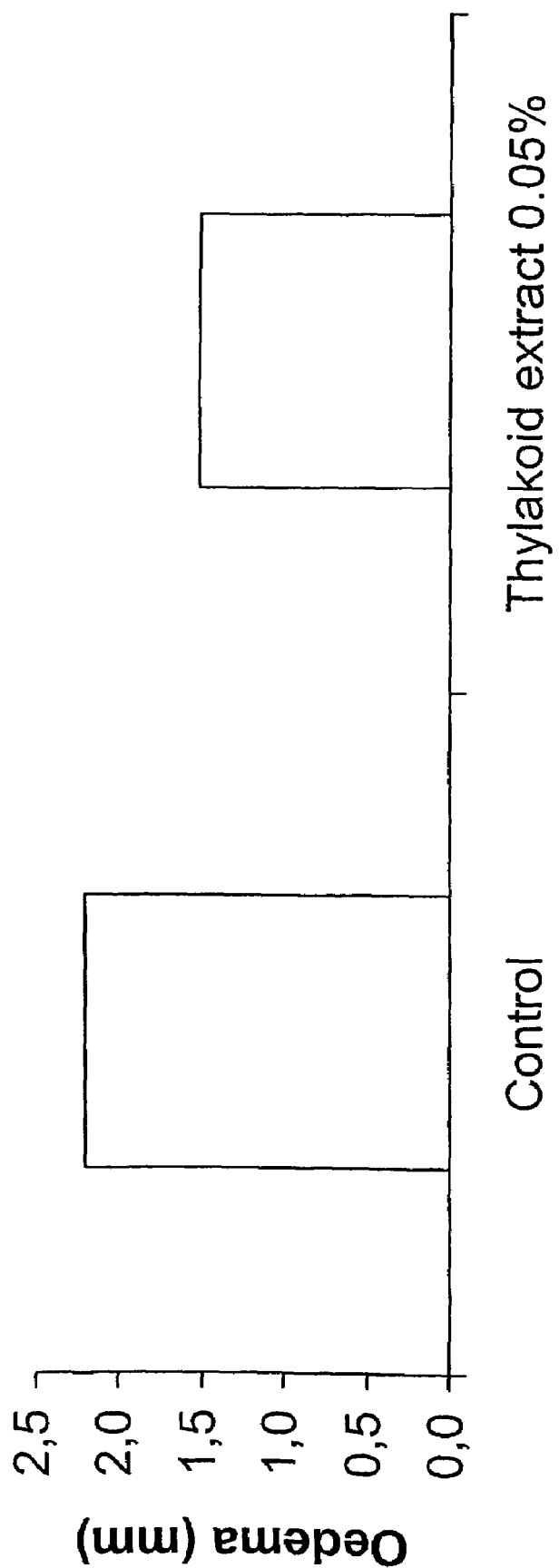
Fig. 14. Effect of intraperitoneal administration of thylakoid extract on rat foot oedema induced by carrageenan

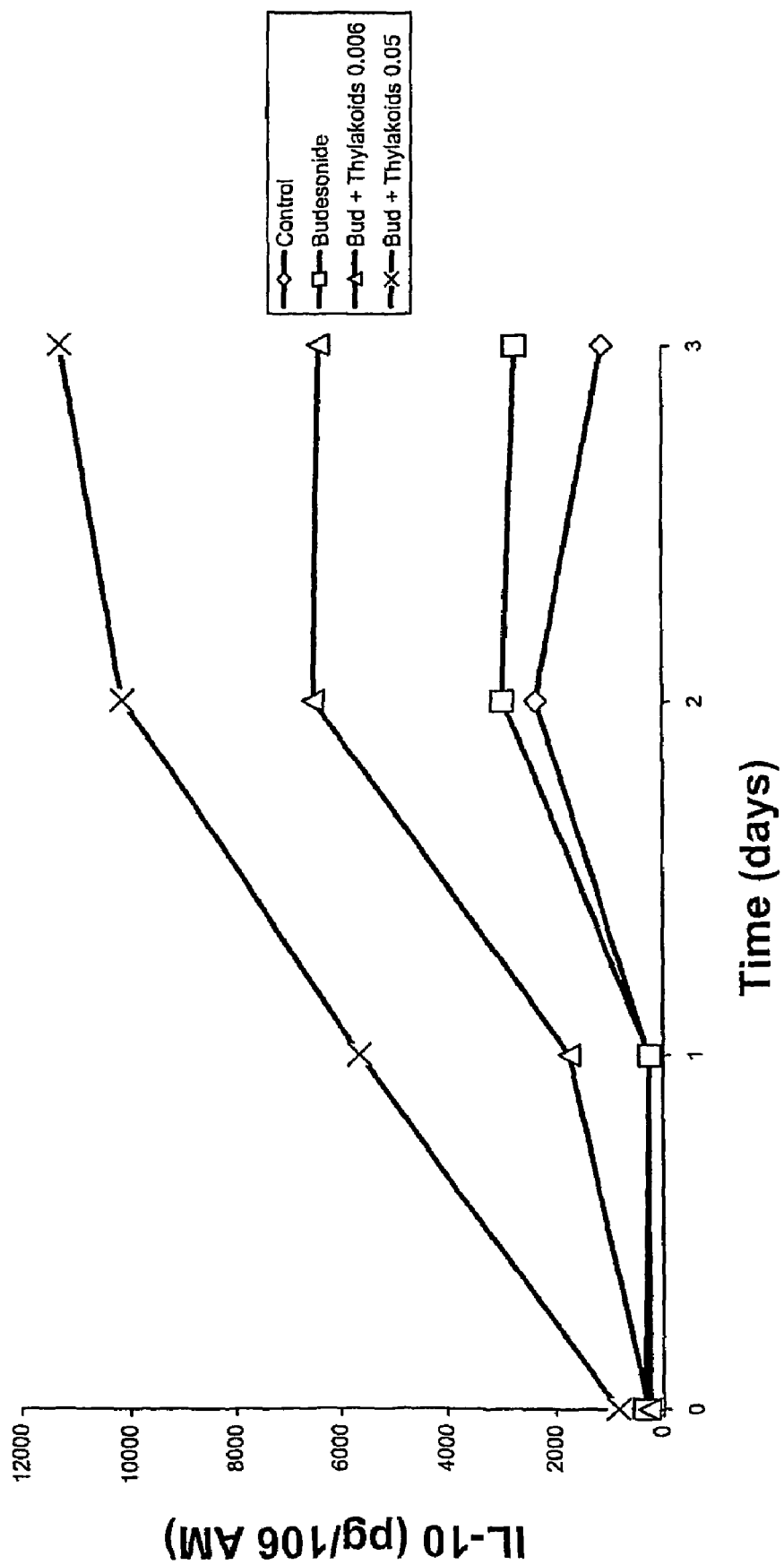

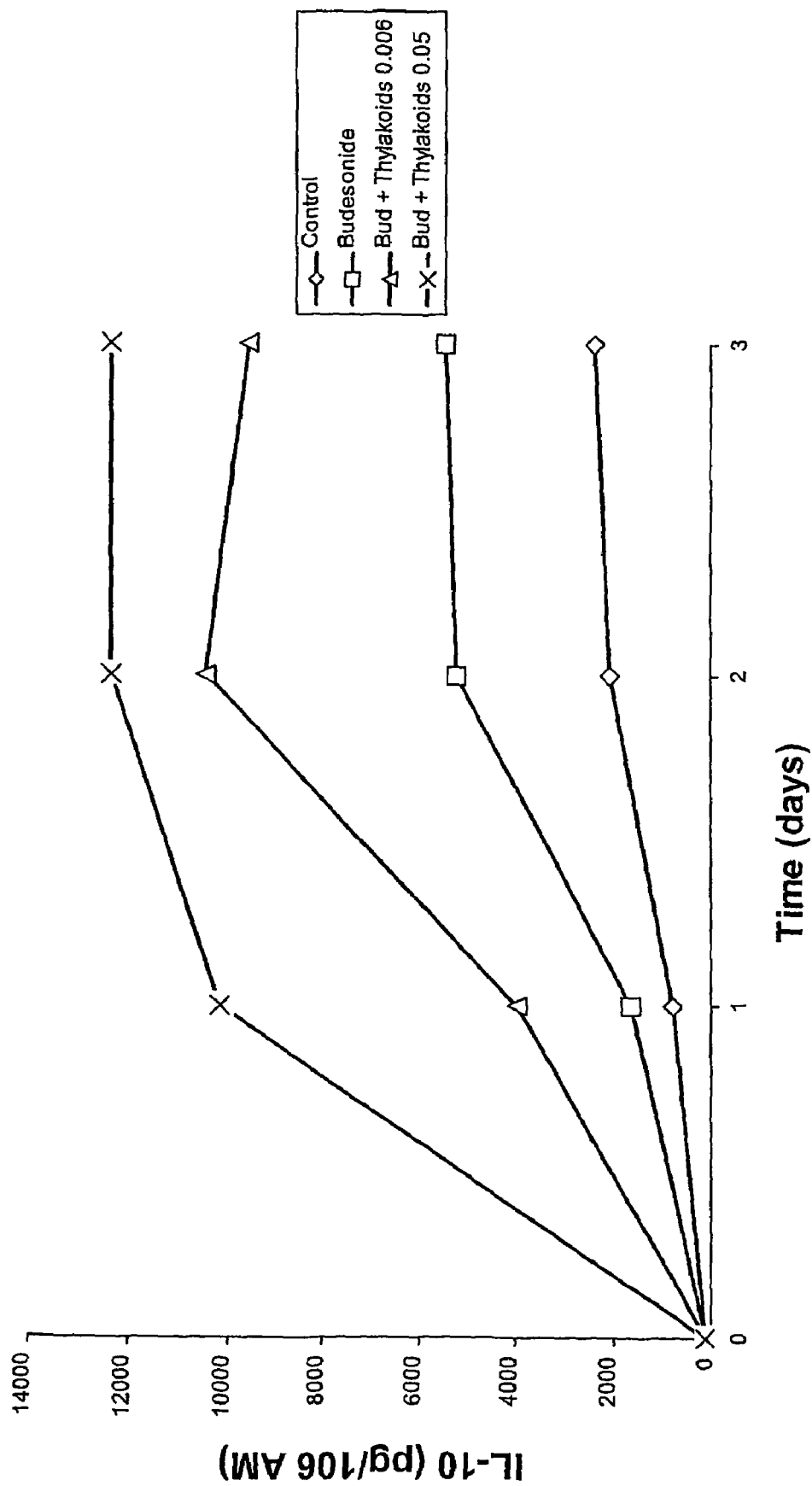
Fig. 16. Effect of post-treatment with thylakoid extract and/or budesonide on IL-10 expression in LPS-stimulated alveolar macrophages

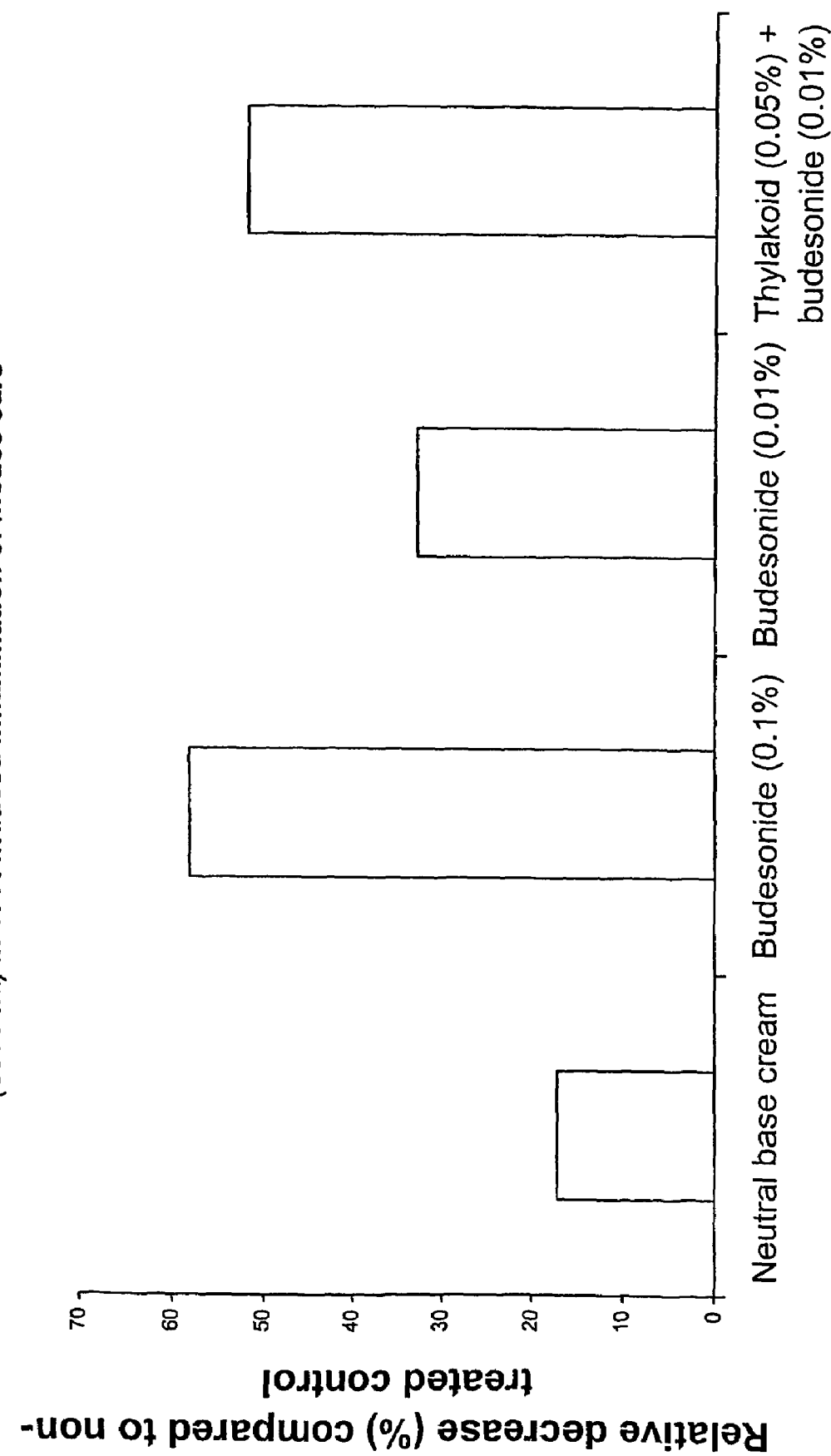
Fig. 17. Potentiation of budesonide by thylakoid extract on the decrease of thickness (oedema) in TPA-induced inflammation of mouse ears

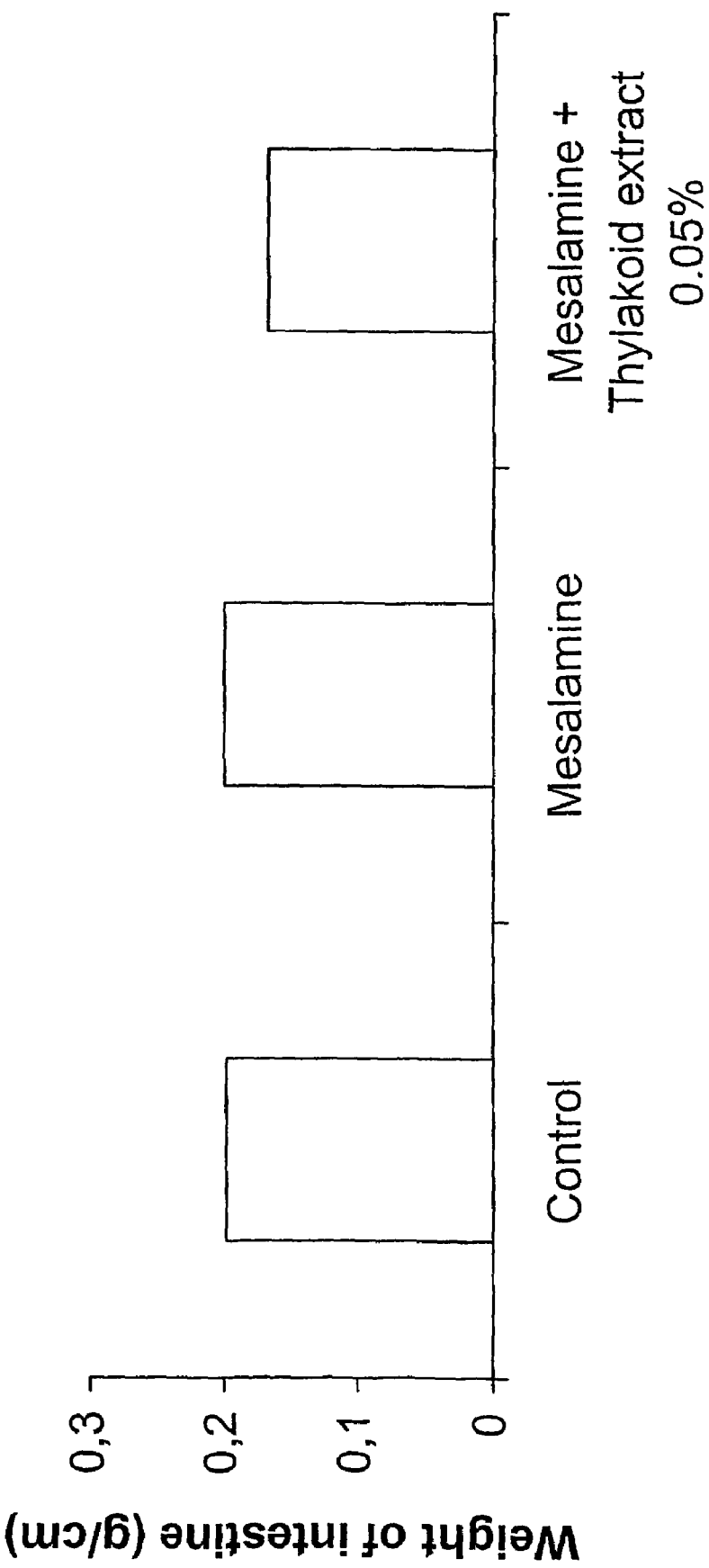
Fig. 18. Effect of thylakoid extract and melasanine of the physical parameters (weight) of inflammed rat intestine

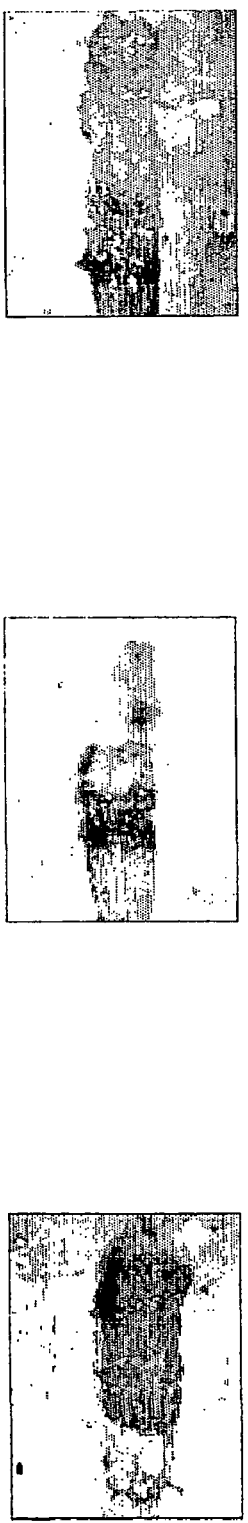

Fig. 19. Effect of the addition of thylakoid extract in the potentiation of mesalamine to reduce TNBS-induced colonic damage Macroscopic colonic damage induced by TNBS stress (control). Average colonic damage = 5.5/10

Effect of mesalamine on intestine damage following TNBS stress. Average colonic damage = 4.0/10

Reduction of membrane alterations by thylakoid extract + mesalamine. Average colonic damage = 3.0/10

COMPOSITIONS COMPRISING THYLAKOIDS USEFUL IN THE MODULATION OF INFLAMMATION PROCESS

CROSS REFERENCE TO RELATED APPLICATIONS

This application is a national phase filing of PCT application No. PCT/CA2002/001009, filed Jul. 2, 2002, which claims priority of Canadian Patent Application No. 2,381,830, filed Apr. 15, 2002. This application further claims the benefit under 35 U.S.C. 119(e) of U.S. provisional application No. 60/301,832, filed Jul. 2, 2001. Each of the above-cited applications is incorporated herein by reference in its entirety.

FIELD OF THE INVENTION

The invention relates to the use of compositions comprising thylakoids, in specific formulations that ensure the integrity and stability of said thylakoids, to regulate or inhibit inflammation, through their modulating activity on physical and biochemical parameters of inflammation, particularly cytokines involved in the inflammation process.

BACKGROUND OF THE INVENTION

Inflammation is a process well known for its implication in acute and chronic diseases and disorders in the biomedical field. Although inflammation is a natural process associated with cell and tissue defense and regeneration, disorganized inflammation can contribute to (or is implicated in) many processes that are harmful to cells and tissues.

Inflammation is the body's reaction to infectious agents, antigen challenge or physical, chemical or traumatic injury (Stvrtinova et al., 1995). The main purpose of inflammation is to bring fluids, proteins, and cells from the blood into the damaged tissues. The main features of the inflammatory response are (i) vasodilation (widening of the blood vessels to increase blood flow); (ii) increased vascular permeability that allows diffusible components to enter the tissues; (iii) cellular infiltration by chemotaxic, or directed movement of inflammatory cells through the walls of blood vessels into the site of injury; (iv) changes in biosynthetic, metabolic, and catabolic profiles of the affected tissues; and (v) activation of cells of the immune system as well as enzymatic systems of the blood plasma.

In general, the inflammation response is quite efficient in managing and repairing damages induced by injury or infectious agent. The degree to which these phenomena occur is normally proportional to the severity of the injury or the extent of the challenge. However, inflammation can become harmful to tissues when it develops in a disorganized, disproportionate or undesired manner and can lead to diseases and disorders.

The acute inflammation response is short lasting and involves all of the previously mentioned features of inflammation. Acute inflammation, when it proceeds in a disorganized fashion, can cause many harmful effects such as the digestion/destruction of normal tissues, excessive swelling that may lead to obstruction of blood flow, resulting in ischemia damage, hypersensitive reaction to non threatening entities (e.g. allergens), etc.

The chronic inflammation reaction may be seen as a long-lasting inflammation, where the inflammatory agent is continually present. In this context, chronic inflammation is essentially observed under conditions of delayed hypersensitivity. However, chronic inflammation may be seen is cases where the inflammatory agent is not continuously present, as is the case of in asthma, arthritis or inflammatory bowel disease, and it may also be related to neurological or genetic disorders. In this case, one or more inflammatory components contribute to the etiology and perpetuation of inflammation.

The process of inflammation is driven and modulated by a complex interplay between products of the plasma enzyme systems, lipid mediators (arachidonic acid metabolites such as prostaglandins and leukotrienes), vasoactive mediators released from inflammatory cells, and, in particular, cytokines.

Prostaglandins (derived from eicosanoic essential fatty acids) are produced during an inflammatory response by inflammation-related biochemical pathways and are responsible for mediating the clinical manifestations characteristic of inflammation. The major source for the production of inflammation-related prostaglandins is arachidonic acid. Arachidonic acid can be metabolized by one of two cyclo-oxygenases (COX-1 or COX-2) producing inflammatory metabolites. The increased production of pro-inflammatory metabolites in inflamed tissues is due to the specific up-regulation of COX-2 (Maier et al., 1990). The increased expression of COX-2 during an inflammatory response is believed to be induced (in part) by exposure to bacterial endotoxins and/or the release of pro-inflammatory cytokines (Isakson, 1995; Raz et al., 1989; O'Sullivan et al., 1992), although other materials may increase expression of COX-2 as well.

In contrast, COX-1 is constitutively expressed in most tissues and has been proposed to be involved in the maintenance of physiological functions such as platelet aggregation, cytoprotection in the stomach, and in part, the regulation of normal kidney function (Prasit et al., 1995; Pinto et al., 1995; Whittle et al., 1980).

In addition to the production of pro-inflammatory eicosanoid metabolites via the cyclo-oxygenase pathways, arachidonic acid also serves as the source for the production of another class of inflammation-related metabolites produced by a family of related enzymes called lipoxygenases (LOX). In particular, 5-LOX catalyzes the first step of a biochemical cascade that culminates in the biosynthesis of a class of molecules termed leukotrienes (Sirois, 1985). Leukotrienes have been implicated as important mediators of inflammatory responses, such as anaphylaxis, suggesting that potent inhibitors of 5-LOX would provide an approach to limit the deleterious effects of all the products of this pathway. Elevated 15-LOX activity has been associated with conditions such as asthma and hypereosinophilia. Selective inhibition of 5-, 12-, or 15-LOX may provide an agent with a definite therapeutic advantage.

In addition to prostaglandins and leukotrienes, cytokines also play a critical role in the inflammatory response. They are produced at the onset of inflammation development and are responsible for the eventual outcome of the inflammation process as well as its resolution. When injury or challenge occurs, cytokines are released from inflammatory cells (mast cells, basophils, endothelial cells, macrophages and neutrophils). The release of many different cytokines is activated during this process including the pro-inflammatory interleukins IL-1, IL-6, IL-8, IL-12, and tumor necrosis factor (TNF-α). In order to counteract an exaggerated inflammation, anti-inflammatory cytokines such as IL4, IL-10, IL-13, and transforming growth factor (TGF-β) are also produced.

Although many cytokines are involved in the inflammation process, some cytokines have a central role in the process and have recently been examined as possible targets for anti-inflammatory products.

Acute and chronic inflammation is most often treated with compounds with anti-inflammatory activity. Non-steroidal anti-inflammatory drugs (NSAIDs) such as aspirin are among the most frequently used drugs currently available. Originally, the medicinal utility of classical NSAIDs was suspected to be due to their ability to inhibit the activities of COX-1 (Mitchell et al., 1993; Meade et al., 1993). Today, it is recognized that NSAIDs also have anti-inflammatory activity due to inhibition of COX-2 as well. Other biochemical activities associated with NSAIDs include inhibition of inflammatory mediators other than those mentioned above (i.e. histamine, serotonin, kinins), inhibition of oxidative phosphorylation, displacement of anti-inflammatory peptides from serum albumin, or displacement of peptides that hyperpolarize neuronal membranes in inflamed tissue (Foye, 1989).

The key roles played by arachidonic acid metabolites produced by COX-2 and 5-, 12-, 15-LOX in mediating inflammatory responses has prompted extensive research to identify compounds capable of specifically inhibiting the enzymatic activities of COX-2, 5-, 12-, 15-LOX, or more than one simultaneously (i.e., dual inhibitors). Compounds capable of inhibiting COX-2 (but not COX-1) and/or 5-LOX would be of great use as anti-inflammatory agents without the ensuing deleterious side effects common to most non-steroidal anti-inflammatory drugs. Alternatively, compounds inhibiting release of arachidonic acid or compounds antagonizing pro-inflammatory cytokines would be of potential therapeutic use, whether they are steroidal (SAID), non-steroidal. (NSAID), cytokine suppressive (CSAID) or other anti-inflammatory drugs. Such inhibitory compounds would have great clinical utility in the treatment of such conditions as pain, fever, asthma, allergic rhinitis, rheumatoid arthritis, osteoarthritis, gout, adult respiratory disease syndrome, inflammatory bowel disease, endotoxic shock, ischemia-induced myocardial injury, atherosclerosis, and brain damage caused by stroke. Such inhibitors could also be used topically for the treatment of acne, sunburn, psoriasis, eczema, and related conditions.

Though anti-inflammatory drugs are widely used to effectively treat inflammation, side effects of anti-inflammatory drug use such as steroid resistance, high doses, osteoporosis, catabolism of proteins and lipids, redistribution of lipidic masse, etc. are a major concern in medical research and drug development. One approach to alleviate side effects is to develop anti-inflammatory drug that have specific biochemical targets such as the development of NSAIDs that inhibit COX-2 (but not COX-1).

Although this strategy if current in terms of research and development of anti-inflammatory drugs, an alterative strategy would be to use current anti-inflammatory drugs in combination with a potentiation agent in order to heighten the efficacy of less effective anti-inflammatory drugs and, potentially, lower the dosage rate in order to alleviate some of the side effects.

Cytokines play a critical role in the inflammatory response. They are produced at the onset of inflammation development and are responsible for the eventual outcome of the inflammation process as well as its resolution. When injury or challenge occurs, cytokines are released from inflammatory cells (mast cells, basophils, endothelial cells, macrophages and neutrophils). The release of many different cytokines is activated during this process including the pro-inflammatory interleukins IL-1, IL-6, IL-8, IL-12, and tumor necrosis factor (TNF-$\alpha$). In order to counteract an exaggerated inflammation, anti-inflammatory cytokines such as IL-4, IL-10, IL-13, and transforming growth factor (TGF-$\beta$) are also produced.

Pro- to anti-inflammatory cytokines will determine the eventual outcome of inflammation by their relative proportions, their affinities, and their interactions. More accurately, an appropriate balance and interaction of pro- to anti-inflammatory cytokines will modulate the inflammation process in order to deal with the injury or challenge in the most efficient manner. In order to limit or prevent the damaging effects of inflammation, the immune system is normally well equipped with methods to regulate the balance of pro- and anti-inflammatory cytokines. However, many diseases or disorders will occur when the injured tissue is unable to create this appropriate cytokine balance and interaction (Feghali and Wright, 1997). The onset of the inflammation process is, therefore, not attributable to a single cytokine. For example, an elevation in pro-inflammatory cytokines will not necessarily cause exaggerated inflammation if it is accompanied by an elevation in anti-inflammatory cytokine levels.

Although many cytokines are involved in the inflammation process, some cytokines have a central role in the process and have recently been examined, as possible targets for anti-inflammatory products. For example, the pro-inflammatory cytokine TNF-$\alpha$ has been clearly established as playing a pivotal role in many chronic inflammatory diseases and has been targeted for such therapies as monoclonal antibodies, soluble TNF-$\alpha$ receptors, TNF-converting enzyme, and other anti-TNF-$\alpha$ therapies (Lewis and Manning, 1999).

The anti-inflammatory cytokine IL-10 also plays a critical role in the inflammation process to down-regulate the acute inflammation response. Because of this property, IL-10 has been actively studied as a therapeutic means of controlling inflammation related diseases through gene therapy (Lewis and Manning, 1999; Sacca et al., 1997).

A thylakoid extract that has anti-oxidant properties, as described in the patent publication WO01/49305 has been tested for its capacity as a modulator of cytokines, and in combination with other anti-inflammatory agents. This extract is provided in the form of specific formulations that ensure the integrity and stability thereof. To simplify terminology, the terms "thylakoids", "thylakoid extract", and "extract" are used hereinbelow and are meant to cover all the specific formulations comprising thylakoids.

TNF-$\alpha$ and IL-10 have been selected as preferred examples of cytokines that are systematically involved in inflammation, notwithstanding the nature of the causative agent or the nature of the tissue or system.

There is an increasing body of literature suggesting that these two cytokines are involved in the expression of inflammatory diseases and disorders exemplified but not limited to those affecting the following tissues:

Skin: psoriasis (Reich et al., 2001), cutaneous inflammation (Berg et al., 1995), atopic dermatitis (Lee et al., 2000);
Brain: encephalitis (Deckert et al., 2001);
Gastrointestinal tract: inflammatory bowel disease (Gasche et al., 2000), Crohn's disease (Narula et al., 1998), colitis (Moriguchi et al., 1999);
Eye: infected cornea (Yan et al., 2001);
Lung: hypersensitivity pneumonitis (Gudmundsson et al., 1998), chronic lung inflammation (Jones et al., 1996);
Multiorgan: ischemia-reperfusion injury (Daemen et al., 1999);

Autoimmune disease: rheumatoid arthritis (Maini et al., 1997; van Roon et al., 1996); and Hyper-reactivity: asthma (Thomas, 2001).

The state of the art and the availability of a performing and stabilized thylakoid extract prompted the present inventors to test the extract against IL-10 and/or TNF-α expression.

Besides the capacity of affecting cytokines expression, the complementarity of the thylakoid extract with other anti-inflammatory agents has been investigated.

SUMMARY OF THE INVENTION

The present invention relates to the use of a thylakoid extract, in nutraceutical, cosmeceutical, and pharmaceutical applications, in the modulation of the inflammatory process and, particularly, of the expression of cytokines involved in the inflammatory response, which can cause diseases or disorders stemming from disorganized, disproportionate or undesirable inflammatory response.

This invention more specifically relates to the use of a thylakoid extract as an efficient and long-lasting modulator of both pro- and anti-inflammatory cytokines.

More precisely, the invention relates to the use of a thylakoid extract in the regulation of pro-inflammatory cytokines such as TNF-α and anti-inflammatory cytokines such as IL-10, as well as the relative proportions (balance) between these two cytokines.

Another object of the invention is to provide compositions comprising thylakoids and an anti-inflammatory agent. Preferred embodiments of anti-inflammatory agents are glucocorticoids or NSAIDs, examples of which are budesonide and mesalamine, respectively.

Other objects, advantages and features of the present invention will become more apparent upon reading of the following non restrictive description of preferred embodiments thereof, given by way of example only with reference to the accompanying drawings.

The contents of the documents cited in the present disclosure are incorporated by reference thereto.

DETAILED DESCRIPTION OF THE INVENTION

The thylakoid extract is an active extract obtained from photosynthetic organisms, which has the ability to modulate the inflammatory process and, particularly, to modulate inflammatory cytokines and/or their balance in tissues submitted to stresses that induce an inflammatory response. In particular, the thylakoid extract has demonstrated its competence in the modulation of the pro-inflammatory cytokine TNF-α and the anti-inflammatory cytokine IL-10, thus providing protection against the damages caused by the inflammatory response or, conversely, increasing an immune response to improve the body's reaction against a danger (such as a tumor or an intruder) or a stress agent.

The thylakoid extract of the present invention is described in patent publication WO01/49305. This extract is defined as one obtained by a process comprising the steps of:

a) providing a suspension of photosynthetic organism constituents that contain thylakoids;

b) disrupting the constituents while recovering thylakoids under light conditions which minimize light flux, in a medium having a viscosity comprised between 1 to 1.3 centipoise and a pH above 2 and below 10; the medium being added in a volume calculated upon the following equation:

$$\frac{(\text{Volume of medium} + \text{organism constituents water content})}{\text{Organism constituents dry weight}} > 10, \text{ preferably } 25\text{-}100,$$

whereby a first extract essentially constituted of thylakoids, cells debris/membranes, and a liquid phase is obtained, said thylakoids comprising organized photosynthetic pigments in their fundamental state;

c) separating thylakoids, cell debris/membranes and liquid phase from each another, to form a second, third and fourth extracts essentially constituted by isolated thylakoids, cell debris/membranes, and a liquid phase, respectively; and d) eliminating any electron donor from the first, second and third extracts so as to stabilize the photosynthetic pigments in their fundamental state.

In this process, the pH is preferably comprised between 5 and 8, namely between 6 and 7.5.

The organism is preferably a plant.

The suspension of step a) is obtained by mechanically dispersing plant constituents or tissues in said medium.

The step a) is preceded by a step of submitting a plant to a conditioning parameter selected from light, osmotic stress, heat, cold, freezing, dryness, hormones, chemical and biological inducers. Preferably, the step of conditioning is a light environment of a wavelength comprised between about 500 and 600 nm, and step b) is performed under the same light conditions.

In the process, the viscosity is partly achieved by adding a sugar in the medium. Sorbitol is such a sugar that has been used in a concentration of about 0.2 to 1.5 M in the medium. Any other sugar achieving a viscosity equivalent to 0.2 to 1.5 M sorbitol is contemplated. The sorbitol concentration that has been particularly preferred is 0.2 to 0.4 M.

The medium namely has the following composition: Tris or acetate or ascorbate buffer (20 mM) having a pH of 7.5 or sorbitol or sucrose or fructose 350 mM.

In the process, the step of separating is performed upon a difference of sedimentation coefficient of each of thylakoids, cell debris and membranes, and liquid phase.

This step of separating namely comprises centrifuging the first extract in a tube equipped with a filter in a superior portion of the tube, the filter having a porosity onto which cell debris and membranes deposit while the thylakoids and the liquid phase pass through the filter, the thylakoids forming a pellet in an inferior portion of the tube.

The electron donor which is withdrawn at the end of the process is usually water.

Water is eliminated under vacuum freeze drying.

Alternatively, water is eliminated by exchanging it against an amphoteric solvent or surfactant after step c). The amphoteric solvent is preferably propylene glycol.

Performing this process results in the obtention of an extract comprising purified functional photosynthetic pigments in their thylakoid membrane environment.

The extract is composed of substantially pure thylakoids free of electron donor, the photosynthetic chlorophyll and carotenoid pigments thereof being stabilized in their integral and fundamental state and ratio to maximize the absorption and dissipation of energy and to protect the extract against oxidative damages.

The thylakoid extract is considered as a modulator of cytokine balance. Such a balance involves, on the one hand, pro-inflammatory cytokines that may comprise TNF-α, and, on the other hand, anti-inflammatory cytokines that may comprise IL-10. A modification of this balance accompanies other biological, biochemical, and/or physiological evidence of inflammation damage following stress induced by inflammatory agents such as physical, traumatic or infectious agents.

The thylakoid extract is particularly considered to significantly prevent or alleviate the damage due to disorganized inflammation through the modulation of inflammatory cytokines in favor of anti-inflammatory cytokines.

The thylakoid extract can regulate the inflammatory response through the modulation of pro- and anti-inflammatory cytokines at concentrations of 0.00005 to 5%. Generally, topical formulations would comprise from 0.1 μg to 1 mg of extract per $cm^2$ of skin or mucosae. Maximum efficacy is obtained with 0.001 to 0.1% thylakoid extract for an application of 2 μl per $cm^2$, which provides an effective amount of 2 μg to 200 μg of extract per $cm^2$ of surface. Furthermore, systemic formulations would comprise from 0.00005 to 500 mg of extract per kg of weight. Maximum efficacy is obtained with 0.001 to 0.1% thylakoid extract which provides an effective amount of 0.05 to 5 mg of extract per kg of weight. This extract is used to prevent or alleviate symptoms of inflammation damage to a degree that is comparable or superior to that of recognized anti-inflammatory therapies/products.

The thylakoid extract can be further combined to other anti-inflammatory agents. The use of the extract in a combined therapy may take different forms (co-applied, co-formulated or sequentially administered with one or more of the complementary anti-inflammatory agents). Such anti-inflammatory agents include but are not limited to molecules such as peptides (bradykinin antagonists, for example), anti-adhesion molecules (anti-LFA-1 or anti-ICAM-1 antibodies, for example), anti-inflammatory extracts of natural (animal (e.g. cartilage, milk), plant, microbe, algae, mineral (e.g. zinc, gold), for example), or synthetic origin, immunosuppressants, glucocorticoids, steroids, non-steroidal anti-inflammatory drugs or NSAIDs, cytokine suppressive anti-inflammatory drugs, anti-ischemics, nitric oxide inhibitors, hypoglycemiants, cromogl cate, anti-histaminics, adrenergics, xanthins, leucotriene receptor antagonists, protease and other enzyme inhibitors (e.g. specific COX-2 and- LOX inhibitors, dual LOX/COX inhibitors, phospholipase A2 inhibitors, NADPHoxidase inhibitors, adenosine kinase inhibitors), septic shock inhibitors, anti-oxidants (vitamins, glutathione . . . ) and nicotine. An impressive list of compounds can be found in U.S. Pat. No. 6,407,135 as anti-inflammatory candidates.

The doses of these anti-inflammatory agents are those known in the literature or lower. Such combination may aim at reducing the dose of a drug that produces undesirable side effects, or at increasing the efficacy of a drug without increasing the severity of the side effects.

This invention will be described hereinbelow, referring to specific embodiments and the appended figures, the purpose thereof being to illustrate this invention rather than to limit its scope.

BRIEF DESCRIPTION OF THE DRAWINGS

FIG. 1. Effect of thylakoid extract on cytokine expression (% relative to control) in alveolar macrophages when induced with LPS FIG. 2. Effect of pretreatment with thylakoid extract on IL-10 expression in LPS-stimulated alveolar macrophages FIG. 3. Effect of post-treatment with thylakoid extract on IL-10 expression in LPS-stimulated alveolar macrophages FIG. 4. Effect of pre-treatment with thylakoid extract on TNF-alpha expression in LPS-stimulated alveolar macrophages FIG. 5. Effects of post-treatment with thylakoid extract on TNF-alpha expression in LPS-stimulated alveolar macrophages FIG. 6. Effect of thylakoid extract on the physical parameters of rat ear oedema following inflammation induced by arachidonic acid FIG. 7. Effect of thylakoid extract on the physical parameters of mouse ear oedema following inflammation induced by TPA FIG. 8. Effect of thylakoid extract on the physical parameters (thickness) of TPA-induced mouse ear inflammation FIG. 9. Effect of thylakoid extract on myeloperoxidase release in TPA-induced mouse ear inflammation FIG. 10. Effect of thylakoid extract on TNF-α expression in mouse skin following inflammation induction by UV-irradiation FIG. 11. Effect of intraperitoneal administration of thylakoid extract on weight of rat intestine induced by TNBS FIG. 12. Effect of thylakoid extract on reducing TNBS-induced colonic damage FIG. 13. Effect of thylakoid extract on the physical parameters of DSS-induced intestine inflammation FIG. 14. Effect of intraperitoneal administration of thylakoid extract on rat foot oedema induced by carrageenan FIG. 15. Effect of pre-treatment with thylakoid extract and/or budesonide on IL-10 expression in LPS-stimulated alveolar macrophages FIG. 16. Effect of post-treatment with thylakoid extract and/or budesonide on IL-10 expression in LPS-stimulated alveolar macrophages FIG. 17. Potentiation of budesonide by thylakoid extract on the decrease of thickness (oedema) in TPA-induced inflammation of mouse ears FIG. 18. Effect of thylakoid extract and mesalamine of the physical parameters (weight) of inflamed rat intestine FIG. 19. Effect of the addition of thylakoid extract in the potentiation of mesalamine to reduce TNBS-induced colonic damage

EXAMPLES

1. Modulation of the Inflammatory Process and Cytokine Balance

A. In Vitro Models:

Evaluation of Thylakoid Extract on Cytokine Production in Alveolar Macrophages

The alveolar macrophage is one of the major inflammatory cells of the lung and plays an important role in a variety of diseases (Crystal, 1991). The macrophage protects the lung by regulating inflammatory and immune responses through cytokine production. However, these cytokines may also cause the tissue injury associated with many inflammatory diseases of the lung (Crystal, 1991).

Lipopolysaccharides (LPS), a major component of the outer membrane of Gram-negative bacteria is a potent activator of monocytes/macrophages that induces production of several cytokines, including the pro-inflammatory cytokine tumor necrosis factor (TNF-α) and anti-inflammatory cytokine interleukin-10 (IL-10) (Barnes and Lim, 1998).

Inflammatory stimuli activate the transcription of nuclear factor κB (NFκB), resulting in the increased transcription of many inflammatory genes and the release of inflammatory mediators from macrophages such as TNF-α. The same stimuli cause the delayed synthesis of IL-10, which inhibits the expression of these inflammatory-system genes, thus terminating the inflammatory response (Barnes and Lim, 1998).

In asthma, a chronic inflammatory disease of the airways, the IL-10 signal is reduced, leading to increased, lasting, and more pronounced inflammation.

Experiment 1: The use of thylakoid extracts on TNF-α and IL-10 expression in alveolar macrophages induced by LPS.

Protocol 1:

Rat alveolar macrophages (cell line NR8383) were treated with thylakoid extracts (0%, 0.0006%, 0.003%, and 0.006%) in the presence of 10 ng/ml LPS for 20 hours. TNF-α and IL-10 contents were measured using an immunoassay kit for rat TNF-α and IL-10 (BioSources, Camarillo, Calif.).

Results:

TNF-α demonstrated a slight increase (less than 15%), when compared to the control, in all thylakoid concentrations used in this study (FIG. 1). IL-10 revealed a significant increase in expression when compared to the control. IL-10 expression was increased by a minimum of 137% and as much as 162% for the 0.0006 and 0.006% thylakoid treatments, respectively (FIG. 1).

Discussion and Conclusions:

The thylakoid extract has clearly demonstrated its modulation ability in cytokine expression and balance on alveolar macrophages. The thylakoid extract produced a limited increase (less than 15%) of the pro-inflammatory cytokine TNF-α while stimulating IL-10 expression greater than 2-fold, when compared to the control. Overall, these results confirmed a shift in cytokine balance towards the anti-inflammatory cytokine (IL-10) when compared to TNF-α, demonstrating its potential as an inflammation modulator.

Protocol 2.

Sprague-Dawley rat alveolar macrophages (cell line NR8383) were treated with thylakoid extracts (0%, 0.006%, 0.05%) in both an 18-h pre- and 18-h post-treatment in the presence of 100 ng/ml LPS (*Salmonella enteritidis;* Sigma Chemical Co.) for various time periods (24, 48, and 72 h) at 37° C. IL-10 and TNF-α levels were measured in cell free supernatants using ELISA kits for rats (Pharmingen, San Diego, Calif.).

Results

Results demonstrated that thylakoid extract stimulated the release of IL-10 in a dose-dependent manner when given in pre- and post-treatment to LPS (FIGS. 2 and 3). In contrast, TNF-α release was reduced by pre-treatment with thylakoid extract (FIG. 4), whereas TNF-α release was not affected by a post treatment (FIG. 5).

Conclusions

These data suggest that thylakoid extract possesses cytokine modulation properties and has the ability to shift the balance of inflammatory cytokines towards anti-inflammatory cytokines such as IL-10.

The above-observed effects on alveolar macrophages lead to the assumption that the thylakoid extract is useful to treat a disease or disorder involving macrophages, or in the making of a medication for such a purpose. By simple extrapolation, it is even possible to envisage that a dose capable of achieving about 1 μg to 100 mg of the extract per liter of body fluid (plasma, blood, extracellular water or total body water content, depending on the distribution) could be effective for systemic purposes. A dose in the milligram range per liter of volume of distribution would be preferred.

B. In Vivo Models:

Evaluation of Topical Application of Thylakoid-comprising Cream on Physical and Biochemical Parameters of Skin Inflammation As previously mentioned, acute inflammation is associated with numerous diseases and disorders. Among these diseases and disorders are skin inflammation that produces physiological observable characteristics such as redness and oedema, which are accompanied by biochemical parameters such the regulation of inflammatory cytokines. Recognized means of evaluating acute inflammation and cytokine regulation are comparative studies involving treatments that induce inflammatory stress such as with arachidonic acid, which is a lipidic mediator of the inflammatory response, or phorbol 12-myristate 13-acetate (Griswold et al., 1998) or such as with ultraviolet (UV) rays (Brink et al., 2000).

Experiment 2: The ability of the thylakoid extract in reducing or preventing the physical signs of inflammation was investigated on rat ears with arachidonic acid as the inflammation stress inducer.

Protocol:

Male Wistar rats (Charles River laboratories) were kept in individual cages, at 20° C. and 55% relative humidity with 12-h light/12-h dark cycle, in a facility that met the Canadian Council on Animal Care (C.C.A.C.) guidelines. The rats were subjected to an 18-hour starving period prior to treatments;

Three groups of rats were treated in the following manner:

(Treatment 1) No application of cream (n=3);

(Treatment-2) Neutral base cream (n=3);

(Treatment-3) Thylakoid extract (0.01%) in neutral base cream (n=3).

All treatments were applied 16 hours, 8 hours, and 1 hour prior to the inflammatory stress (pretreatment) at a dose of 2 μl/cm$^2$ (20 μg/cm$^2$).

Following treatment, rat ears were subjected to an inflammatory stress by a topical application of arachidonic acid (Sigma Chemicals Co.). 30 μL of arachidonic acid (0.01 mg/μL) in an acetone solution was applied. The arachidonic acid solution was reapplied 15 minutes after the initial application (Griswold et al., 1998). The right ear of each rat was treated with arachidonic acid whereas the left ear served as the unstressed control.

After one hour, the rats were sacrificed and a punch of 6 mm in diameter of both the left and right ears was sampled. Ear punch thickness was measured by an electronic digital caliper 0.01 mm (Traceable).

Results:

Arachidonic acid application caused an inflammatory effect in rat ears that were revealed by the presence of redness and oedema.

Results of oedema parameters indicate that thickness of rat ear punches decreased with a preventive application of thylakoid extracts. When compared with average ear punch thickness of the thylakoid extract treatment (treatment 3), there was an increase of 138.0% of thickness of the non-protected ear (Treatment-1) and an 89.6% increase of ear thickness in the neutral base cream (Treatment-2) (FIG. 6).

Discussion and Conclusions:

The thylakoid extract has an effect on the physical parameters associated with inflammation. The thylakoid extract reduces swelling of rat ears. Theses results suggest that the thylakoid extract has a protective effect towards inflammation.

Experiment 3. Evaluation of thylakoid extract on the physical parameters of inflammation of skin inflammation induced with TPA.

Mice (BALB/C) were kept in individual cages, at 20° C. and 55% relative humidity with 12-h light/12-h dark cycle, in a facility that met the Canadian Council on Animal Care (C.C.A.C.) guidelines. The animals were subjected to an 18-hour starving period prior to treatments.

Three groups of mice were treated in the following manner:
(Treatment 1) No application of cream (n=3);
(Treatment-2) Neutral base cream (n=3);
(Treatment-3) Thylakoid extract (0.05%) in neutral base cream (n=3).

All treatments were applied 16 hours, 8 hours, and 1 hour prior to the inflammatory stress (pre-treatment) at a dose of 2 µl/cm$^2$.

Following treatment, mouse ears were subjected to an inflammatory stress by a topical application of phorbol 12-myristate 13-acetate (TPA) (Sigma Chemicals Co.). 20 µL of TPA (0.2 µg/µL) in an acetone solution was applied (Griswold et al., 1998). The right ear of each mouse was treated with TPA whereas the left ear served as the unstressed control.

After one hour, the mice were sacrificed and a punch of 6 mm in diameter of both the left and right ears was sampled. Ear punch thickness was measured by an electronic digital caliper 0.01 mm (Traceable).

Results:

TPA application caused an inflammatory effect in mouse ears that were revealed by the presence of redness and oedema.

Results of oedema parameters indicate that thickness of mouse ear punches decreased with a preventive application of thylakoid extracts. When compared with the average ear punch of the thylakoid extract treatment (Treatment-3), there was a 8-fold increase in thickness in the neutral base cream treatment (Treatment-2) (FIG. 7).

Discussion and Conclusions:

Pre-treatment with thylakoid extract has an effect on the physical parameters associated with inflammation. The thylakoid extract reduces TPA-induced swelling of rat ears.

Experiment 4. Evaluation of thylakoid extract on the physical and biochemical parameters of inflammation of skin inflammation induced with TPA in absence of light.

Mice (BALB/C) were kept in individual cages, at 20° C. and 55% relative humidity with 12-h light/12-h dark cycle, in a facility that met the Canadian Council on Animal Care (C.C.A.C.) guidelines. The mice were subjected to an 18-hour starving period prior to treatments.

Three groups of animals were treated in the following manner:
(Treatment-1) No application of cream (n=3);
(Treatment-2) Neutral base cream (n=3);
(Treatment-3) Thylakoid extract (0.05%) in neutral base cream (n=3).

All treatments were applied 4 and 8 hours following the inflammatory stress (post-treatment) at a dose of 2 µl/cm$^2$. Animals were kept in the dark for the duration of the treatments.

Prior to treatment, mouse ears were subjected to an inflammatory stress by a topical application of phorbol 12-myristate 13-acetate (TPA) (Sigma Chemicals Co.). 20 µL of TPA (0.2 µg/µL) in an acetone solution was applied (Griswold et al., 1998). The right ear of each mouse was treated with TPA whereas the left ear served as the unstressed control.

After 24 hours, the mice were sacrificed and a punch of 6 mm in diameter of both the left and right ears was sampled. Ear punch thickness was measured by an electronic digital caliper 0.01 mm (Traceable). Tissue samples were assessed biochemically for the neutrophil marker enzyme, myeloperoxidase (MPO), using the method of Romay et al. (1998). Ear tissue was homogenized, submitted to 3 cycles of freezing/thawing, and centrifuged (2500 g for 30 min at 4° C.) and the resulting supernatant was assayed spectrophotometrically for MPO. The change in absorbance at 460 nm was measured. MPO activity data are presented as delta of absorbance (degradation of hydroperoxide).

Results:

Results of oedema parameters indicate that thickness of mouse ear punches decreased with post-treatment with thylakoid extracts. When compared with the average ear punch of the thylakoid extract treatment (Treatment-3), there was a 26.5% increase in thickness in the neutral base cream treatment (Treatment-2) and a 52.8% increase in the non-treated, stressed control (Treatment-1)(FIG. 8). MPO assays revealed that there was a 109.7% increase in MPO release in the non-treated control (Treatment-1) when compared to the thylakoid protected treatment (Treatment-3) (FIG. 9).

Conclusions

Post-treatment with thylakoid extract has an effect on the physical and biochemical parameters associated with inflammation. The thylakoid extract reduces TPA-induced swelling of mouse ears. Furthermore, thylakoid extract significantly reduced MPO release, a measure of neutrophil activation, demonstrating its ability to decrease the inflammatory response.

Experiment 5: The ability of the thylakoid extract in reducing or preventing the physical and biochemical signs of inflammation was investigated in mouse dorsal skin with UVA and UVB as the inflammation stress inducer.

Protocol:

Hairless mice (5 weeks old) were purchased from Charles River Laboratories (Wilmington, Mass.). Mice were housed at the Animal Facility of the Institute for Biological Sciences (IBS) and maintained under standard conditions (23±1° C., 42±6% relative humidity, 12:12-h light-dark cycle). Lights were automatically switched on daily at 7 AM and switched off daily at 7 PM. Mice were fed Purina chow diet (24% protein, 4% fat, and 4.5% fiber) and water ad libitum.

Mice were randomly assigned into irradiation and treatment groups as follows:
Group I: UV-irradiated animals pre-treated with a preparation of topical ointment containing the thylakoid extract (n=5).
Group II: Animals received topical application of the cream containing the thylakoid extract during UV irradiation (post-treated) (n=5).
Group III: UV-irradiated animals (n=5) treated with the preparation of topical ointment without the thylakoid extract.
Group IV: Control A: UV-irradiated animals without any topical treatment (n=5).

Group V: Control B; Non-irradiated animals without any topical treatment (n=5).

Mice were treated with 0.1% thylakoid-comprising cream for a final application of 2 μL/cm² (200 μg/cm²).

The mice were placed in a plastic cage without a lid. Two Westinghouse FS40 sunlamps (spectral irradiance: 280-400 nm, 80% UVB and 20% UVA). Black ray ultraviolet meter was used for the measurement of intensity of light. The fluence at 60 cm from the dorsal surface of the mice was 0.48-0.50 mJ/cm². The mice were given a single exposure of 200 mJ UV light/cm² (acute dosage) for 10 min. This approach has been adopted to take into account minor differences in UV absorption characteristics (optical density differences) in 290-320 nm range that might optically affect UV light irradiation conditions.

After irradiation treatments, mice were kept under the conditions mentioned above for one week. Epidermal observation and photographs were taken to assess redness and dryness.

All the mice from each of the 5 groups were sacrificed. 1 cm² skin was then removed from each mouse and kept in liquid nitrogen. Two skin pieces from each group were ground in liquid nitrogen and the powder was dissolved in RIPA buffer containing a cocktail of protease and phosphatase inhibitors. The samples were homogenized in a mechanical homogenizer at 4° C. and centrifuged at 2500 rpm for 5 min at 4° C. The supernatants were used as cytosolic extracts to study the expression of various epidermal markers.

Samples containing 35 μg total proteins were subjected to protein separation by electrophoresis and the proteins were transferred on nitrocellulose membranes. Western blots were analyzed following immuno-staining with antibodies against TNF-α (rabbit polyclonal antibody; Santa Cruz Biotechnology Inc.).

Results:

Results of skin irritation are summarized in Table 1. Irradiated mice with a pre- or post-treatment of the thylakoid extract showed no skin irritation or symptoms of inflammation whereas irradiated mice without the extract (with or without neutral base cream) exhibited redness and dry skin.

TABLE 1

Effect of 0.1% thylakoid-comprising cream on the physical symptoms of UV-irradiated mice

| Treatment | Symptoms |
| --- | --- |
| Pre-treated with thylakoid extract, irradiated | None |
| Post-treated with thylakoid extract, irradiated | None |
| Neutral cream base, irradiated | Redness and dry skin |
| Untreated, irradiated (Control A) | Redness and dry skin |
| Untreated, non irradiated (Control B) | None |

Following irradiation, TNF-α was less abundant in both pre- and post-treated thylakoid extract treatments when compared to the non treated or neutral base cream treated mice (FIG. 10). The expression of the pro-inflammatory cytokine TNF-α in the thylakoid extract treated groups (groups 1 and 2) is similar to those of the non-stressed control B, while it was increased by 150.0% and 185.7% in irradiated skin of animals non treated with the thylakoid extract (group 3), when compared to the pre- and post-treatments with thylakoid extract, respectively.

Discussion and Conclusions:

The thylakoid extract protected the animals from UV irradiation damages. Even after one week, the non-protected irradiated mice continued to demonstrate redness and skin irritation whereas none of the thylakoid extract treated mice demonstrated these symptoms.

The thylakoid extract clearly exerted a protective effect against inflammation induced by UV-irradiation of exposed mouse skin. It lowers the level of the pro-inflammatory cytokine TNF-α in irradiated mouse skin to a non-irradiated level.

Evaluation of Thylakoid Extract on the Physical Parameters of Inflammation in Rat Intestine Inflammatory Bowel Disease (IBD) is a term used to describe a collection of diseases that involve the bowel and are characterized by the production of chronic inflammation and at times ulceration in the small or large bowel. IBD is genetically determined by an overactive immune response. A defect in gut barrier function and/or immune deregulation appears to mediate this response (Sartor, 1998). This reflects the importance of balance between inflammatory and anti-inflammatory forces, and it correlates clinically with disease severity (Dionne et al., 1998). Among other events, TNF-alpha is stimulated and massive epithelial cell hyperplasia occurs (Higgins et al., 1999). For example, Crohn's disease (a particular case of IBD) is associated with increased TNF-alpha and other inflammatory cytokine levels (Kmiec, 1998), leading to cytokine imbalance. IBD can be stimulated by recognized inflammatory agents such as trinitrobenzensulfonic acid (TNBS) through rectal administration of TNBS/ethanol enema or dextran sulfate sodium (DSS) in distilled drinking water (Kirsner and Shorter, 1995).

Experiment 6. Evaluation of thylakoid extract on the physical parameters of TNBS-induced inflammation in rat intestine Protocol:

Male Wistar rats (Charles River Laboratories, Montreal) were kept in individual cages, at 20° C. and 55% relative humidity with 12-h light/12-h dark cycle, in a facility that met the Canadian Council on Animal Care (C.C.A.C.) guidelines. The rats were subjected to a 24-hour starving period prior to inflammatory stress induction.

Three groups of rats were treated in the following manner:

(Treatment 1) Non-stressed control (n=3);

(Treatment-2) Stressed control: 2,4,6-Trinitrobenzene-sulfonic acid (stress agent) in the intestinal lumen (n=3);

(Treatment-3) Intra-peritoneal administration of thylakoid extract (0.05%), in 1 ml of saline solution (0.9%), 24 and 48 hours prior to administration of the stress agent in the intestinal lumen (n=3).

Twenty-four hours later, the rats were sacrificed and a 10 cm excision of the intestine was sampled. Samples were weighed and macroscopic colonic damage was scored by the following scale:

0 No damage

1 Localized hyperemia, no ulcers

2 Ulcerations without hyperemia of bowel wall thickening

3 Ulceration with inflammation at one site

4 Two or more sites of ulceration/inflammation

5 Major sites of damage extending more than 1 cm along the length of colon 6-10 If damage extends more than 2 cm along length of colon, score is increased by one for each additional 1 cm Results A 50.0% relative increase in intestine weight was observed in the stressed intestine when compared to the thylakoid-protected treatment (FIG. 11). Moreover, TNBS colonic damage was reduced from 5.5 to 2.5 (see scoring chart) when protected with an intra-peritoneal administration of thylakoid extract (FIG. 12).

Conclusions

Intra-peritoneal administration (2 mg/kg) of thylakoid extract has the ability to modulate the physical parameters of intestine inflammation by decreasing inflammation (weight) of stressed intestine and reducing/eliminating macroscopic evidence of hyperemia and ulceration.

Experiment 7. Evaluation of thylakoid extract on the physical parameters of DSS-induced inflammation in rat intestine Protocol:

Male Wistar rats (Charles River Laboratories, Montreal) were kept in individual cages, at 20° C. and 55% relative humidity with 12-h light/12-h dark cycle, in a facility that met the Canadian Council on Animal Care (C.C.A.C.) guidelines.

Four groups of rats were treated in the following manner:
(Treatment 1) Non-stressed control (n=3);
(Treatment-2) Stressed control: dextran sulphate sodium (DSS; stress agent) in drinking water for a 5-day period (n=3);
(Treatment-3) Control treatment: Intra-peritoneal administration of saline solution (0.9%) daily for 5 days (n=3);
(Treatment4) Intra-peritoneal administration of thylakoid extract (0.05%) in 1 ml saline solution (0.9%) daily for 5 days (n=3).

After the five-day period of treatments, the rats were sacrificed and a 10 cm excision of the intestine was sampled and weighed.

Results

DSS caused chronic inflammation of rat intestine. Intestine weight increased by 21.4% in the control (treatment-3) when compared to the treatment containing 0.05% of thylakoid extract (treatment-4) (FIG. 13).

Conclusions:

Following a 5-day chronic inflammation stress with DSS, thylakoid extract (2 mg/kg) was able to significantly reduce the physical manifestation of rat intestine inflammation.

Experiment 8. Evaluation of thylakoid extract on the physical parameters of carrageenan-induced rat foot inflammation (oedema)

Protocol:

Male Sprague-Dawley rats (250 g), which had fasted overnight (18h), received an intra-peritoneal injection of thylakoid extract 0.1% (in 1 ml of 0.9% saline) 1 h prior to subplantar injection of carrageenan (0.1 ml of 1% suspension in 0.9% saline) in the right hind paw. The second dose of thylakoid extract was administrated simultaneously to the carrageenan injection (Romay et al., 1998).

Paw thickness was measured from ventral to dorsal surfaces, with a dial calliper, immediately prior to carrageenan injection and 5 h later. Oedema was expressed as the increase in paw thickness (in mm) measured after carrageeran injection and compared to the preinjection value for the individual animals.

Results

Non-protected rat demonstrated a 45.7% increase in foot oedema when compared to the thylakoid protected treatment (FIG. 14).

Conclusions

In a classic carageenan test, thylakoid extract (4 mg/kg) protected against the physical manifestation of foot oedema.

2. Potentiation of Anti-inflammatory Drugs

A. In Vitro

Experiment 9. Evaluation of thylakoid extract on the potentiation of budesonide in alveolar macrophages Protocol Sprague-Dawley rat alveolar macrophages (cell line NR8383) were treated with thylakoid extracts (0%, 0.006%, 0.05%) and/or budesonide (1 nM; corticoid) in both an 18-h pre- and 18-h post-treatment in the presence of 100 ng/ml LPS (*Salmonella enteritidis;* Sigma Chemical Co.) for various time periods (24, 48, and 72 h) at 37° C. IL-10 levels were measured in cell free supernatants using ELISA kits for rats (Pharmingen, San Diego, Calif.).

Results

Results demonstrated that thylakoid extract stimulated the release of IL-10 when given in pre- and post-treatment to LPS in a synergistic and dose-dependent manner in combination with budesonide (FIGS. 15 and 16).

Conclusions

These data suggest that thylakoid extract possesses cytokine modulation properties and potentiates the effect of corticoid anti-inflammatory agents.

Budesonide contributes in the long term maintenance of high IL-10 levels, which provides a better anti-inflammatory effect.

B. In Vivo

Experiment 10. Evaluation of thylakoid extract on the potentiation of budesonide in mouse ears Mice (BALB/C) were kept in individual cages, at 20° C. and 55% relative humidity with 12-h light/12-h dark cycle, in a facility that met the Canadian Council on Animal Care (C.C.A.C.) guidelines. The animals were subjected to an 18-hour starving period prior to treatments.

Three groups of mice were treated in the following manner:
(Treatment-1) No application of cream (n=3);
(Treatment-2) Neutral base cream (n=3);
(Treatment-3) Budesonide (0.1%) in neutral base cream (n=3);
(Treatment-4) Budesonide (0.01%) in neutral base cream (n=3);
(Treatment-5) Budesonide (0.01%)+thylakoid extract (0.05%) in neutral base cream (n=3).

All treatments were applied 4 and 8 hours following the inflammatory stress (post-treatment) at a dose of 2 µl/cm$^2$. Animals were kept in the dark for the duration of the treatments.

Prior to treatment, mouse ears were subjected to an inflammatory stress by a topical application of phorbol 12-myristate 13-acetate (TPA) (Sigma Chemicals Co.). 20 µL of TPA (0.2 µg/µL) in an acetone solution was applied (Griswold et al., 1998). The right ear of each mouse was treated with TPA whereas the left ear served as the unstressed control.

After 24 hours, the mice were sacrificed and a punch of 6 mm in diameter of both the left and right ears was sampled. Ear punch thickness was measured by an electronic digital caliper 0.01 mm (Traceable).

Results:

Budesonide 0.1% (Treatment-3) decreased the thickness of mouse ear punches by 58.2% when compared to the untreated control (Treatment-1). Budesonide 0.01% (Treatment4) decreased thickness by 32.6%. When thylakoid extract 0.05% was co-applied with budesonide 0.01% (Treatment-5), the decrease in ear punch thickness was 51.8% when compared to the untreated control (Treatment-1). Results are presented in FIG. 17.

Conclusions:

Thylakoid extract 0.05% potentiates the effect of budesonide. When thylakoid extract was co-applied with budesonide 0.01%, the combined effect was equivalent to a dose of budesonide that was 10-times higher (0.1%).

Experiment 11. Evaluation of thylakoid extract on the potentiation of mesalamine in rat intestines Male Wistar rats (Charles River Laboratories, Montreal) were kept in individual cages, at 20° C. and 55% relative humidity with 12-h light/12-h dark cycle, in a facility that met the Canadian Council on Animal Care (C.C.A.C.) guidelines. The rats were subjected to a 24-hour starving period prior to inflammatory stress induction.

Four groups of rats were treated in the following manner:
(Treatment-1) Non-stressed control (n=3);
(Treatment-2) 2,4,6-Trinitrobenzenesulfonic acid (inflammatory agent) in the intestinal lumen (n=3);
(Treatment-3) Mesalamine (5-aminosalicyclic acid; NSAID) (57 mg/kg) administered directly in the intestinal lumen 24 and 48 hours prior to administration of the stress agent (n=3)
(Treatment4) Thylakoid extract (0.05%) (2 mg/kg)+mesalamine (57 mg/kg) administered directly in the intestinal lumen 24 and 48 hours prior to administration of the stress agent (n=3).

Twenty-four hours later, the rats were sacrificed and a 10 cm excision of the intestine was sampled. Samples were weighed and macroscopic colonic damage was scored by the following scale:

The above results indicate that different types of inflammatory diseases models respond to the thylakoid extract alone or in combination with other anti-inflammatory agents.

0 No damage
1 Localized hyperemia, no ulcers
2 Ulcerations without hyperemia of bowel wall thickening
3 Ulceration with inflammation at one site
4 Two or more sites of ulceration/inflammation
5 Major sites of damage extending more than 1 cm along the length of colon
6-10 If damage extends more than 2 cm along length of colon, score is increased by one for each additional 1 cm Results A 19.7% relative increase in intestine weight was observed in the mesalamine-protected intestine when compared to the combined protection of mesalamine and thylakoid extract (FIG. 18). Moreover, colonic damage was reduced from 4.0 to 3.0 (see scoring chart) when thylakoid extract was added to mesalamine in the intestinal lumen (FIG. 19).

Conclusions

The addition 2 mg of thylakoid extract in the intestinal lumen per kg animal body weight has the ability to complete the effects of mesalamine by decreasing inflammation (weight) of stressed intestine and reducing macroscopic evidence of hyperemia and ulceration. Decreasing the doses of mesalamine should confirm that the thylakoid extract potentiates mesalamine-induced effects.

The above results indicate that different types of inflammatory disease models respond to the thylakoid extract alone or in combination with other anti-inflammatory agents. In view of the foregoing results, the thylakoids extract is useful for the treatment of inflammation caused by a diversity of pro-inflammatory stimuli or of etiological components.

Although the present invention has been described hereinabove by way of preferred embodiments thereof, it can be modified, without departing from the spirit and nature of the subject invention as defined in the appended claims.

REFERENCE

Barnes, P G, and Lim, S. 1998. Inhibitory cytokines in asthma. Mol. Med. Today. October pages 452-458.

Berg D J, Leach M W, Kuhn R, Rajewsky K, Muller W, Davidson N J, Rennick D. 1995. Interleukin 10 but not interleukin 4 is a natural suppressant of cutaneous inflammatory responses. J Exp Med. 182:99-108.

Brink, N, Szamel, M, Young, A R, Wittern, K P, and Bergemann, J. 2000. Comparative quantification of IL-10 β, IL-10, IL-10r, TNF-α and IL-7 mRNA levels in UV-irradiated human skin in vivo. Inflamm. Res. 49:290-296.

Crystal, R G. 1991. Alveolar macrophages. In: Crystal, R G and Weast, J B, (eds). The lung: Scientific Foundation. Raven Press, NY. Pages 527-538.

Daemen, M A, van de Ven, M W, Heineman, E, Buurman, W A. 1999. Involvement of endogenous interleukin-10 and tumor necrosis factor-alpha in renal ischemia-reperfusion injury. Transplantation 67:792-800.

Deckert M, Soltek S, Geginat G, Lutjen S, Montesinos-Rongen M, Hof H, Schluter D. 2001. Endogenous Interleukin-10 Is Required for Prevention of a Hyperinflammatory Intracerebral Immune Response in Listeria monocytogenes Meningoencephalitis. Infect Immun. 69:4561-4571

Dionne S, D'Agata I D, Hiscoft J, Vanounou T, Seidman E G. 1998. Colonic explant production of IL-1 and its receptor antagonist is imbalanced in inflammatory bowel disease (IBD). Clin Exp Immunol 112:435-442.

Feghali, C A, and Wright, T M. 1997. Cytokines in acute and chronic inflammation. Front. Biosci. 1:d12-26.

Foye, W O. 1989. Principals of Medicinal Chemistry. Lea and Febiger, London.

Gasche C, Bakos S, Dejaco C, Tillinger W, Zakeri S, Reinisch W. 2000. IL-10 secretion and sensitivity in normal human intestine and inflammatory bowel disease. J Clin Immunol. 20:362-70.

Griswold, D E, Martin, L D, Badger, A M, Breton, J, and Chabot-Fletcher, M. 1998. Evaluation of the cutaneous anti-inflammatory activity of azaspiranes. Inflamm. Res. 47:56-61.

Gudmundsson, G, Bosch, A, Davidson, B L, Berg, D J, Hunninghake, G W. 1998. Interleukin-10 modulates the severity of hypersensitivity pneumonitis in mice. Am. J. Repir. Cell. Mol. Biol. 19:812-818.

Higgins LM, Frankel G, Douce G, Dougan G, MacDonald TT. 1999. Citrobacter rodentium infection in mice elicits a mucosal Th 1 cytokine response to lesions similar to those in murine inflammatory bowel disease. Infect Immun 67:3031-3039.

Isakson, P. C. 1995. Med. Chem. Res. 5:344.

Jones, C A, Cayabyab, R G, Kwong, K Y, Stofts, C, Wong, B, Hamdan, H, Minoo, P, deLemos, RA. 1996. Undetectable interleukin (IL)-10 and persistent IL-8 expression early in hyaline membrane disease: a possible developmental basis for the predisposition to chronic lung inflammation in preterm newborns. Pediatr. Res. 39:966-975.

Kirsner J B, Shorter R G. 1995. Inflammatory Bowel Disease. Chapter 3: 4th Edition; Williams and Wilkins, Maryland.

Kmiec Z. 1998. Cytokines in inflammatory bowel disease. Arch Immuno Ther Exp (Warsz) 46:143-155.

Lee H J, Lee H P, Ha S J, Byun D G, Kim J W. 2000. Spontaneous expression of mRNA for IL-10, GM-CSF, TGF-beta, TGF-alpha, and IL-6 in peripheral blood mononuclear cells from atopic dermatitis. Ann Allergy Asthma Immunol. 84:553-558.

Lewis, A J and Manning, A M. 1999. New targets for anti-inflammatory drugs. Curr. Opin. Chem. Biol. 3:489-494.

Maier, J. A. M., Hla, T., Macaig, T. J. 1990. J. Biol. Chem. 265:10805.

Maini, R N, Elliot, M, Brennan, F M, Williams, R O, Feldmann, M. 1997. TNF blockade in rheumatoid arthritis: implications for therapy and pathogenesis. APMIS 105:257-263.

Meade, L A, Smith, W I, DeWitt, D L. 1993. J Biol Chem 268:6610.

Mitchell, J A, Akarasereenont, P, Thiemermann, C, Flowers, R, Vane, J R. 1993. P.N.A.S. 90:11693.

Moriguchi M, Urabe K, Norisada N, Ochi C, Staic A, Urleb U, Muraoka S. 1999. Therapeutic effects of LK 423, a phthalimido-desmuramyl-dipeptide compound, on dextran sulfate sodium-induced colitis in rodents through restoring their interleukin-10 producing capacity. Arzneimittelforschung. 49:184-192.

Narula S K, Cutler D, Grint P. 1998. Immunomodulation of Crohn's disease by interleukin-10. Agents Actions Suppl. 49:57-65. Review.

O'Sullivan, M. G., Chilton, F. H., Huggins, E. M., McCall. E. 1992. J. Biol. Chem. 267:14547.

Pinto, D. J., Pitts, W. J., Copeland, R. A., Covington, M. B., Trzaskos, J., Magolda, R. 1995. Med. Chem. Res. 5:394.

Prasit, P., Black, C. C., Chan, A. W., Ford-Hutchinson, J. Y., Gauthier, R., Gordon, D., Guay, S., Kargman, C. K., Lau, C. S., Li, J., Mancini, N., Quimet, P., Roy, P., Tagari, P., Vickers, E., Wong, R. N., Young, and R. Zamboni. 1995. Med. Chem. Res. 5:364.

Raz, A., Wyche, A., Needleman, P. 1989. P.N.A.S. 86:1657.

Reich K, Garbe C, Blaschke V, Maurer C, Middel P, Westphal G, Lippert U, Neumann C. 2001. Response of psoriasis to interleukin-10 is associated with suppression of cutaneous type 1 inflammation, downregulation of the epidermal interleukin-8/CXCR2 pathway and normalization of keratinocyte maturation. J Invest Dermatol. 116:319-329.

Romay C, Ledon N, Gonzalez R. 1998. Further studies on antiinflammatory activity of phycocyanin in some animal models of inflammation. lnflamm. Res. 47:334-338, 1998.

Sacca, R, Cuff, C A, and Ruddle, N H. 1997. Mediators of inflammation. Curr. Opin. Immunol. 9:851-857.

Sartor R B. 1998. The role of indigenous microflora in producing inflammation in inflammatory bowel disease. Research and Clinical Forum 20:117-123.

Sirois, P. 1985. Pharmacology of the leukotrienes, Advances in Lipid Research, R. Paoletti, D. Kritchevsky (eds.) Academic Press, 21:79.

Stvrtinova, V, Jakubovsky, J, Hulin, I. 1995. Inflammation and fever. Academic Electronic Press, Bratislava, Slovak Republic. 113 p.

Thomas, P S. 2001. Tumor necrosis factor-alpha: The role of this multifunctional cytokine in asthma. Immunol Cell Biol. 79:132-140 van Roon, J A, van Roy, J L, Gmelig-Meyling, F H, Lafeber, F P, Bijlsma, J W. 1996. Prevention and reversal of cartilage degradation in rheumatoid arthritis by interleukin-10 and interleukin4. J. Rheumatol. 39:829-835.

Whittle, B. J. R., Higgs, G. A., Eakins, K. E., Moncada, S., and Vane, J. R. 1980. Nature 284:271.

Yan X T, Zhuang M, Oakes J E, Lausch R N. 2001. Autocrine action of IL-10 suppresses proinflammatory mediators and inflammation in the HSV-1 -infected cornea. J Leukoc Biol. 69:149-157.

What is claimed is:

1. A method for modulating an inflammatory process in a subject, said method comnrising administering an effective amount of a thylakoid extract and an an effective amount an anti-inflammation agent to said subiect to modulate the inflammatory process.

2. The method of claim 1, comprising modulating an amount of (a) pro-inflammatory cytokines, (b) anti-inflammatory cytokines or (c) both (a) and (b) induced during the inflammatory process.

3. The methoduse of claim 2, wherein said pro-inflammatory cytokines comprise tumor necrosis factor-alpha (TNF-α).

4. The method of claim 2, wherein said anti-inflammatory cytokines comprise interleukin-10.

5. The method of claim 2, wherein the amount of anti-inflammatory cytokines is increased.

6. The method of claim 1, wherein said anti-inflammatory agent is a glucocorticoid.

7. The method of claim 1, wherein said anti-inflammatory agent is a non-steroidal anti-inflammatory drug (NSAID).

8. The method of claim 1, wherein the extract is administered at a dose of about 0.00005 to 500 mg per kg of a subject's body weight.

9. The method of claim 1, wherein the extract is administered at a dose of about 0.05 to 5 mg per kg of a subject's body weight.

10. The method of claim 1, wherein the administration is topical.

11. The method of claim 10, wherein said administration comprises about 0.1 µg to 1 mg of extract per cm$^2$ of surface of a subject's skin or mucosae.

12. The method of claim 10, wherein said administration comprises about 1 µg to 200 µg of extract per cm$^2$ of surface of a subject's skin or mucosae.

13. A composition to inhibit inflammation in a subject, comprising an effective amount of an anti-inflammatory agent and an effective amount of a thylakoid extract.

14. The composition of claim 13, wherein said anti-inflammatory agent is a glucocorticoid.

15. The composition of claim 13, wherein said anti-inflammatory agent is a non-steroidal anti-inflammatory drug (NSAID).

16. The composition of claim 13, which is topical.

17. The composition of claim 16, wherein said effective amount of extract is about 0.1 μg to 1 mg per cm² of surface of a subject's skin or mucosae.

18. The composition of claim 16, wherein said effective amount of extract is about 1 μg to 200 μg per cm² of a subject's surface of skin or mucosae.

19. The composition of claim 13, wherein said effective amount of extract is about 0.00005 to 500 mg per Kg of a subject's body weight.

20. The composition of claim 13, wherein said effective amount of extract is about 0.05 to 5 mg per Kg of a subject's body weight.

21. The composition of claim 13, wherein said thylakoid extract comprises functional photosynthetic pigments.

22. The composition of claim 16, wherein said effective amount of extract is about 0.00005 to 5%.

* * * * *